(12) United States Patent
John et al.

(10) Patent No.: US 9,309,536 B2
(45) Date of Patent: Apr. 12, 2016

(54) RECOMBINANT VIRUS-LIKE PARTICLES ENCODED BY MULTI-GENE VECTOR

(71) Applicant: Pfizer Inc., New York, NY (US)

(72) Inventors: Corinne John, Horgen (CH); Christian Schaub, Wadenswil (CH); Sabine Wellnitz, Urdorf (CH)

(73) Assignee: PFIZER INC., New York, NY (US)

( * ) Notice: Subject to any disclaimer, the term of this patent is extended or adjusted under 35 U.S.C. 154(b) by 0 days.

(21) Appl. No.: 14/472,911

(22) Filed: Aug. 29, 2014

(65) Prior Publication Data
US 2015/0004690 A1 Jan. 1, 2015

Related U.S. Application Data

(62) Division of application No. 13/318,221, filed as application No. PCT/EP2010/055943 on Apr. 30, 2010, now abandoned.

(30) Foreign Application Priority Data

May 1, 2009 (EP) .................................. 09159287

(51) Int. Cl.
*C12N 15/86* (2006.01)
*C12N 7/00* (2006.01)
*A61K 39/00* (2006.01)

(52) U.S. Cl.
CPC *C12N 15/86* (2013.01); *C12N 7/00* (2013.01); *A61K 2039/5256* (2013.01); *A61K 2039/5258* (2013.01); *C12N 2710/14143* (2013.01); *C12N 2710/16123* (2013.01); *C12N 2710/20023* (2013.01); *C12N 2710/20034* (2013.01); *C12N 2760/16123* (2013.01); *C12N 2760/16134* (2013.01)

(58) Field of Classification Search
None
See application file for complete search history.

(56) References Cited

U.S. PATENT DOCUMENTS

| | | | |
|---|---|---|---|
| 2004/0071709 | A1 | 4/2004 | Rottier et al. |
| 2004/0224305 | A1 | 11/2004 | Wilson et al. |
| 2005/0130127 | A1 | 6/2005 | Rottier et al. |
| 2005/0186575 | A1 | 8/2005 | Rottier et al. |
| 2007/0099262 | A1 | 5/2007 | Anderson et al. |
| 2008/0004228 | A1 | 1/2008 | Berger et al. |
| 2009/0022762 | A1 | 1/2009 | Galarza et al. |

FOREIGN PATENT DOCUMENTS

| | | |
|---|---|---|
| JP | 2007-527722 | 10/2007 |
| WO | 01/97840 | 12/2001 |
| WO | 02/092827 | 11/2002 |
| WO | 2004/092387 | 10/2004 |
| WO | 2005/085456 | 9/2005 |
| WO | 2007/054250 | 5/2007 |
| WO | 2007/130330 | 11/2007 |
| WO | 2009/012489 | 1/2009 |

OTHER PUBLICATIONS

Saikh et al. Influenza A Virus-Specific H-2dRestricted Cross-Reactive Cytotoxic T Lymphocyte Epitope(s) Detected in the Hemagglutinin HA2 Subunit of A/Udorn/72. Virology, 1995, 214: 445-452.*
Latham et al. Formation of wild-type and chimeric influenza virus-like particles following simultaneous expression of only four structural proteins. J Virol. Jul. 2001;75(13):6154-65.*
Crowe et al. Uneven distribution of MHC class II epitopes within the influenza virus. Vaccine. Jan. 23, 2006;24(4):457-67. Epub Aug. 15, 2005.*
Sato et al. Localization of influenza virus proteins to nuclear dot 10 structures in influenza virus-infected cells. Virology. May 25, 2003;310(1):29-40.*
Greenstone et al. Chimeric papillomavirus virus-like particles elicit antitumor immunity against the E7 oncoprotein in an HPV16 tumor model. Proc Natl Acad Sci U S A. Feb. 17, 1998;95(4):1800-5.*
GenBank: ABD79035.1. neuraminidase [Influenza A virus (A/udorn/1972(H3N2))]. Dated Mar. 16, 2006.*
GenBank: AFG98921.1. neuraminidase [Influenza A virus (A/Bilthoven/5931/1974(H3N2))]. Dated Apr. 4, 2012.*
Buonamassa et al. Yeast Coexpression of Human Papillomavirus Types 6 and 16 Capsid Proteins. Virology 293, 335-344 (2002).*
International Search Report issued Sep. 13, 2010 in International (PCT) Application No. PCT/EP2010/055943 along with the Written Opinion.
Australian Office Action dated Jun. 18, 2014 issued in Australian Application No. 2010243489.
Y. L. Zhang et al., "Enhanced Immunogenicity of Modified Hepatitis B Virus Core Particle Fused with Multiepitopes of Food-and-Mouth Disease Virus", Scandinavian Journal of Immunology, vol. 65. No. 4, pp. 320-328, Apr. 1, 2007.
Bryce Chackerian, "Virus-like particles: flexible platforms for vaccine development", Expert Rev. Vaccines, vol. 6. No. 3, pp. 381-390, 2007, XP009163686.
I. Berger et al., "Baculovirus Expression System for Heterologous Multiprotein Complexes", Nature Biotechnology, vol. 22, No. 12, pp. 1583-1587, Dec. 2004.
D. J. Fitzgerald et al., "Protein Complex Expression by Using Multigene Baculoviral Vectors", Nature Methods, vol. 3, No. 12, pp. 1021-1032, Dec. 2006.

(Continued)

*Primary Examiner* — Stacy B Chen
*Assistant Examiner* — Nick Zou
(74) *Attorney, Agent, or Firm* — Wenderoth, Lind & Ponack, L.L.P.

(57) ABSTRACT

The invention describes novel virus-like particles for use as vaccines, diagnostic tools and R&D tools based on recombinant DNA and cell cultivation techniques for production. The recombinant virus-like particles of the invention are assembled by polypeptide chains that incorporate several, in particular two or more, different epitopes which are selected either (a) from different viral strains of the same virus and/or (b) from different serotypes of the same virus and/or (c) from different viral strains specific for different hosts. These epitopes are then displayed on the particle surface.

11 Claims, 8 Drawing Sheets

(56) References Cited

OTHER PUBLICATIONS

T. Kanda et al., "Development of an HPV Vaccine for a Broad Spectrum of High-Risk Types", Human Vaccine, vol. 5, No. 1, pp. 43-45, Jan. 2009.
K. Slupetzky et al., "Chimeric Papillomavirus-Like Particles Expressing a Foreign Epitope on Capsid Surface Loops", Journal of General Virology, vol. 82, pp. 2799-2804, 2001.
A. Varsani et al., "Chimeric Human Papillomavirus Type 16 (HPV-16) L1 Particles Presenting the Common Neutralizing Epitope for the L2 Minor Capsid Protein of HPV-6 and HPV-16", Journal of Virology, vol. 77, No. 15, pp. 8386-8393, Aug. 2003.
Y. Xu et al., "Encapsidating Artificial Human Papillomavirus-16 mE7 Protein in Human Papillomavirus-6b L1/L2 Virus Like Particles", Chinese Medical Journal, vol. 120, No. 6, pp. 503-508, 2007.
M. Zhuang et al., "Coexpression of HPV-16 and -11 L1 Genes using the Bivalent Recombinant Baculovirus and VLPs Assembled by L1 proteins", Chin. J. Microbiol Immunol., vol. 26, No. 9, pp. 771-776, Sep. 2006.
Paz De la Rosa et al., "An HPV 16 L1-based chimeric human papilloma virus-like particles containing a string of epitopes produced in plants is able to elicit humoral and cytotoxic T-cell activity in mice", Virol J.. 2009, vol. 6, No. 2, doi: 10.1186/1743-422X-6-2.
Gallagher et al., "Identification of HLA-DR1- and HLA-DR15-restricted human papillomavirus type 16 (HPV16) and HPV18 E6 epitopes recognized by CD4+ T cells from healthy young women", J Gen Virol., May 2007;vol. 88, Pt 5, pp. 1470-1478.
Hohn et al., "Human papillomavirus type 33 E7 peptides presented by HLA-DR*0402 to tumor-infiltrating T cells in cervical cancer". J Virol.. Jul. 2000, vol. 74, No. 14, pp. 6632-6636.
McCarthy et al., "Definition of an HPV18/45 cross-reactive human T-cell epitope after DNA immunisation of HLA-A2/KB X transgenic mice", Int J Cancer, May 2006, vol. 118, No. 10, pp. 2514-2521.
Luo et al., "Induction of V3-specific cytotoxic T lymphocyte responses by HIV gag particles carrying multiple immunodominant V3 epitopes of gp120", Virology, Jan. 1998, vol. 240, No. 2, pp. 316-325.
Mathiesen et al., "Mapping of IgG subclass and T-cell epitopes on HIV proteins by synthetic peptides", Immunology, Aug. 1989, vol. 67, No. 4, pp. 453-459.
Xu et al., "Papillomavirus virus-like particles as vehicles for the delivery of epitopes or genes", Arch. Virol., vol. 151, 2006, pp. 2133-2148.
Chackerian, "Virus-like particles: flexible platforms for vaccine development", Expert Review Vaccines, vol. 6, No. 3, 2007, pp. 381-390.
Mathiesen et al., "Mapping of IgG subclass and T-cell epitopes on HIV proteins by synthetic peptides", Immunology, vol. 67, 1989, pp. 453-459.
Crevar et al., "Elicitation of protective immune response using a bivalent H5N1 VLP vaccine" Virology Journal, vol. 5, 2008, pp. 1-9.
De la Rosa et al., "An HPV 16 LI-based chimeric human papilloma virus-like particles containing a string of epitopes produced in plants is able to elicit humoral and cytotoxic T-cell activity in mice", Virology Journal, vol. 6, No. 2, 2009, pp. 1-11.
Luo et al., "Induction of V3-Specific Cytotoxic T Lymphocyte Responses by HIV gag Particles Carrying Multiple Immunodominant V3 Eppitopes of gp120", Virology, vol. 240, 1998, pp. 316-325.
Extended European Search Report dated Nov. 6, 2015, issued in parallel European Divisional Application No. 15173061.1.
Torbjorn et al., "Immunotherapeutic polyoma and human papilloma virus-like particles", Immunotherapy, 2009, vol. 1, No. 2, pp. 303-312.
Tang et al., "Baculovirus-Produced Influenza Virus-like Particles in Mammalian Cells Protect Mice from Lethal Influenza Challenge", Viral Immunology, 2011, vol. 24, No. 4, pp. 311-319.

\* cited by examiner

A)

B)

C)

D)

E)

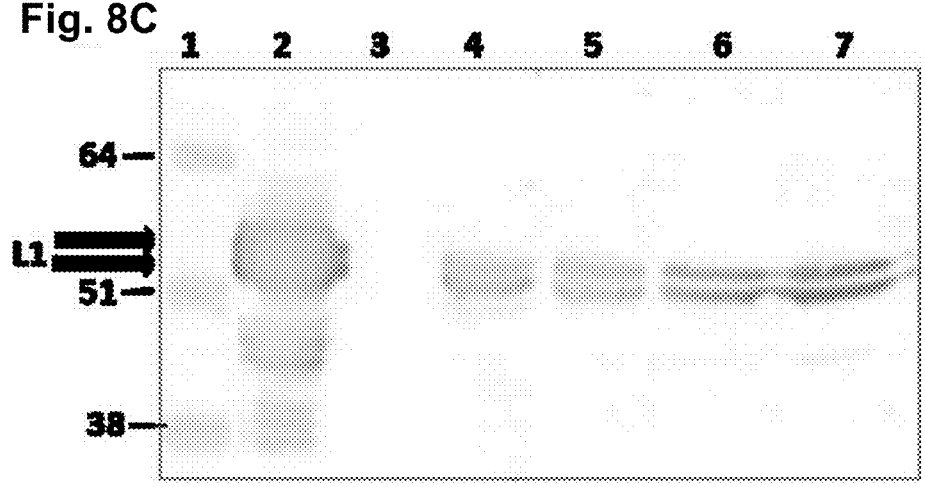

RECOMBINANT VIRUS-LIKE PARTICLES ENCODED BY MULTI-GENE VECTOR

FIELD OF THE INVENTION

The invention relates to recombinant virus-like particles comprising epitopes from different virus strains, and vectors encoding these.

BACKGROUND OF THE INVENTION

There is an increasing interest in small natural biomolecules using them in different aspects in biomedicine, nanotechnology and material science. Virus simulators, virus capsids or virus-like particles are very attractive because of their regular structure, their homogenous particle size, their stability, the ease of production and the potential for manipulation. Virus-like particle possess dynamic structures, their interior is accessible and furthermore the coat is modifiable. Dependent on the application the virus-like particles could have an envelope or not and could be chosen as virus simulators. These embodiments could be used as new biological entities or targets, as vaccines, as antigens for antibody production, as research tools, as diagnostic tool, for drug delivery and bioconjunctions. These virus simulators are formed by self-assembly of envelope and or capsid proteins of many viruses. The size varies between 22-150 nm dependent on the morphology of the particular virus. The virus simulators are non-infectious because they assemble without incorporating genetic material. Dependent on the application foreign genetic material could be included in the herein described virus simulator.

A promising application of these virus simulators is the production of vaccines against various diseases because their repetitive, high density display of epitopes elicit often a strong immune response. The small size of particles is an advantage for uptake by dendritic cells. Chimeric virus simulators offer an enormous potential in selective, multi-epitope, multi-protein, multi-serotype, multi-strain, or multi-species presentation.

There exist many expression systems for the production of virus simulators which include the baculovirus/insect cell system, various mammalian cell lines, either stably or transiently transfected or transduced with viral expression vectors, furthermore various species of yeast including *Saccharomyces cerevisiae* and *Pichia pastoris*, and *Escherichia coli* and other bacteria.

Vaccination is dependent on the generation of a sufficient immunity to protect from infectious diseases. The mostly used attenuated virus vaccines rely on limited replication of the virus in the host following immunization. But this kind of vaccination may cause severe reactions in some patients. Therefore the development of virus-like particles (VLP) as subunit vaccines is an advantage because the particles lack in general DNA or RNA genome but have the authentic conformation of the natural virus.

Vaccination is one of the most potent and cost-effective counter-measures to the threat of e.g. seasonal or pandemic influenza outbreaks. The ease of spread as an aerosol and the cause for a severe illness especially to susceptible humans are the major reasons why influenza is one of the most devastating viral diseases. Currently licensed seasonal vaccines are only partially protective, and the egg-based production is very time-consuming and cost-intensive. This strategy is vulnerable to the unanticipated emergence of epidemic strains that are poorly matched or not matched at all by the vaccine. Due to the danger of emerging strains of avian influenza or influenza of other origin novel vaccine approaches are necessary.

In another aspect the research in the field of several important viruses like HCV, HIV, Ebola etc. is very difficult because of biosafety issues. Until now there exist only a few models for investigation of viral entry and viral trafficking. Diagnostic tools are based on the genome of these viruses because of the lack of appropriate non-infectious virus models.

Presently commercial human influenza vaccines contain hemagglutinin as their only or main viral antigen. Their production starts from viruses grown on embryonated chicken eggs or, more recently, in mammalian cells in tissue culture. The production in eggs requires selection of high yield, reassorted virus strains, is limited in capacity, time-consuming (6-8 months), and expensive. Beyond that it can cause problems in vaccinated persons allergic to egg protein. The production is only possible with non-lethal bird strains. One of the most important disadvantages of the egg-based production is the limited capacity. In case of a pandemic the production of the seasonal influenza vaccine has to be stopped in favour of a pandemic influenza vaccine production which could result in even more lethal events in the long run.

Vaccines against viral diseases rely traditionally on attenuated virus strains or inactivation of infectious virus. An appropriate environment is necessary for highly pathogenic or haemorraghic viruses which constrains the production possibilities because of the biosafety level (e.g. BL3/BL4). For some viruses like human papilloma virus the attenuation will not be sufficient because the virus cannot be propagated in vitro. The ability to generate human papilloma virus (HPV)-like particles based vaccines (Gardasil, Cervarix) has changed the prospects for preventing cervical cancer in woman.

Due to the danger of emerging strains of avian influenza or other origin, novel vaccine approaches are necessary which result in an enhanced protection.

SUMMARY OF THE INVENTION

The invention relates to a recombinant virus-like particle comprising two or more different epitopes or different proteins comprising epitopes which are selected either (a) from different viral strains of the same virus and/or (b) from different serotypes of the same virus and/or (c) from different viral strains specific for different hosts. These recombinant virus-like particles are useful as vaccines, and the invention also relates to these vaccines.

Furthermore the invention relates to a vector comprising two or more polynucleotides coding for different epitopes or for different proteins comprising epitopes which are selected either (a) from different viral strains of the same virus and/or (b) from different serotypes of the same virus and/or (c) from different viral strains specific for different hosts, and to host cells comprising these vectors.

(C) (SEQ ID NO:3) Expression vector construct with embedded epitopes (HA, NA, M1, M2) from influenza B/Florida isolates (D) (SEQ ID NO:4) Vector construct for expression of an epitope (L1) of HPV16 and HPV18 serotypes where both genes are under the control of different promoters (E) (SEQ ID NO:5) Same Vector construct as (B) with deletion of promoter p10

The vectors contain two promoters P1 and P2 (◁,▷) selected from polh, p10 and $p_{XIV}$ very late baculoviral promoters, vp39 baculoviral late promoter, vp39polh baculoviral late/very late hybrid promoter, pca/polh, pcna, etl, p35, egt, da26 baculoviral early promoters; CMV, SV40, UBc. EF-1, RSVLTR, MT, $P_{DS47}$, Ac5, $P_{GAL}$ and $P_{ADH}$ The terminator sequences T1 and T2 (T) are selected from SV40, HSVtk or BGH (bovine growth hormone). Furthermore the vector contains the transposon sites TnL and TnR (L,R) for generation of MultiBacbacmid, a loxP site (LP) for site specific homologous recombination (plasmid fusion), an origin of replication (O), ampicillin (A) and gentamycine (G) resistance genes and defined restriction sites.

Figure 2:
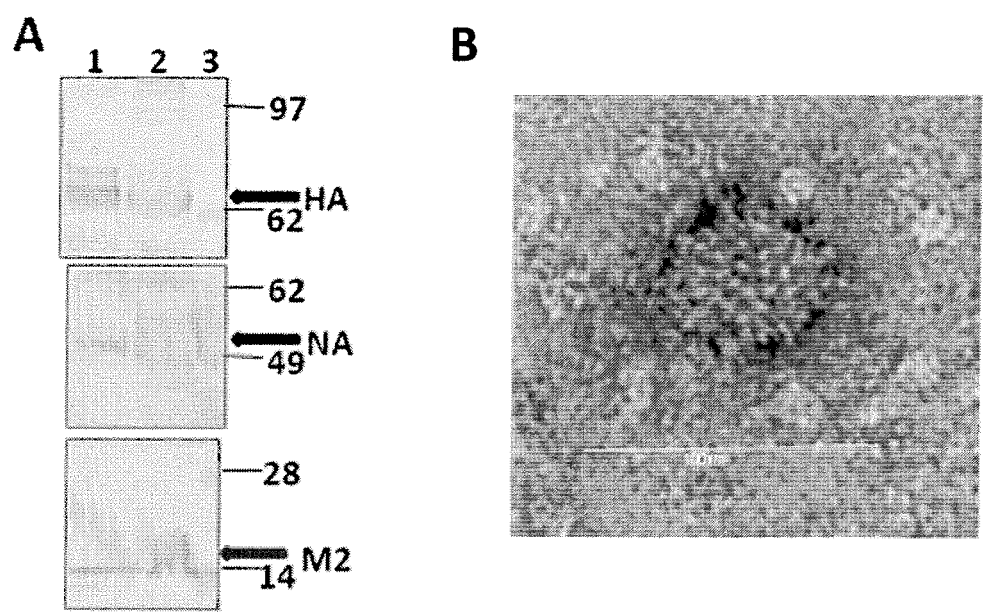

FIG. 2: Analysis of expressed chimeric influenza virus-like particles.

(A) The conformation of secreted (A, lane 2) as well as intracellular VLPs (prepared from SEQ ID NO:1, A, lane 1) is verified by immunoblotting using specific antibodies against the proteins HA (H3), NA (H3) and M2 (H1). Lane 3=ladder, protein sizes in kDa. The epitopes are co-localized, which means that they are assembled in one particle.

(B) Visualization of the chimeric Influenza virus-like particle (prepared from SEQ ID NO:3) by electron microscopy using negative staining with uranyl acetate. The spikes representing epitope HA are visible. The size of the particle is in the range of 50-80 nm.

Figure 3:
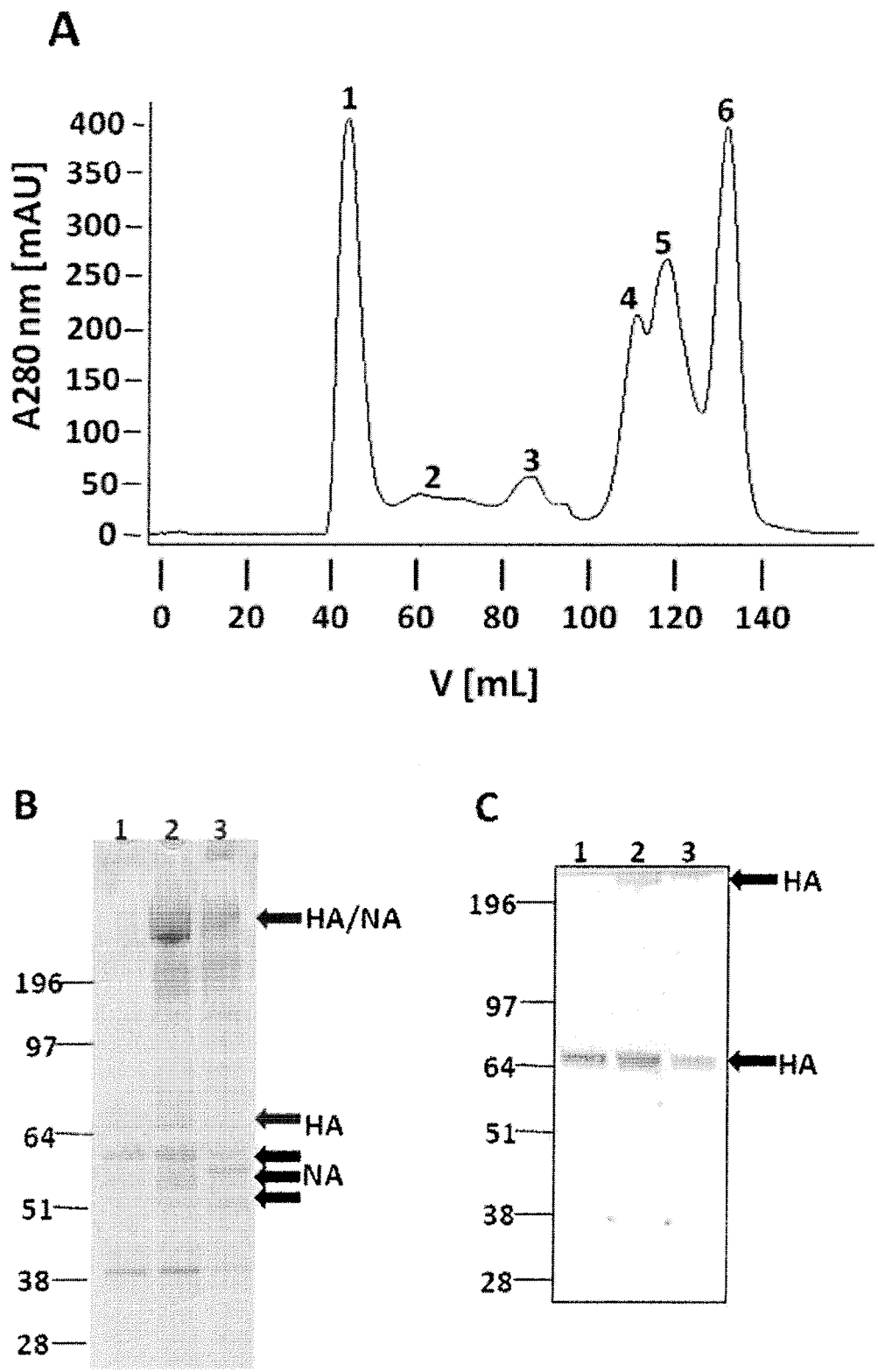

FIG. 3: Chromatographic purification and analysis of secreted multi-epitope influenza virus-like particles prepared from SEQ ID NO:1.

(A) Chromatogram of gel filtration purification. The first peak (1) contains the virus-like particle (VLP). The other peaks (2-6) represent contaminant proteins.

(B) Coomassie-stained SDS-PAGE. The multiple epitopes of the virus-like particles are verified by analyzing different fractions from the $1^{st}$ peak (1) representing the start (lane 1), middle (lane 2) and end (lane 3) part of the VLP containing peak. The ladder [kDa] is represented left of the first lane. Detection of epitopes is indicated by arrows.

(C) Western blot analysis according to Coomassie-stained gel using an anti-HA antibody.

Figure 4:
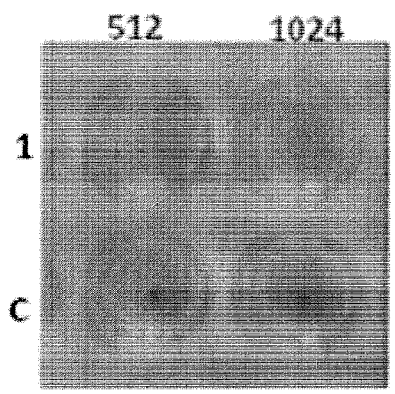

FIG. 4: Functionality of nature-like influenza virus-like particles (VLP).

Twofold serial dilution series (1:2 to 1:2048) of the purified VLPs (prepared from SEQ ID NO:3) are analyzed by standard hemagglutination assay. 50 µL purified particle solution was coated onto 96-well plate incubated with red blood cells (erythrocytes). The influenza VLP (1, upper part) are able to agglutinate red blood cells in a dose dependent manner. Highest dilution is 1:1024. In contrast PBS, used as control (C), leads only to precipitation of erythrocytes, visible as a "dot" in the middle of the well.

Figure 5:
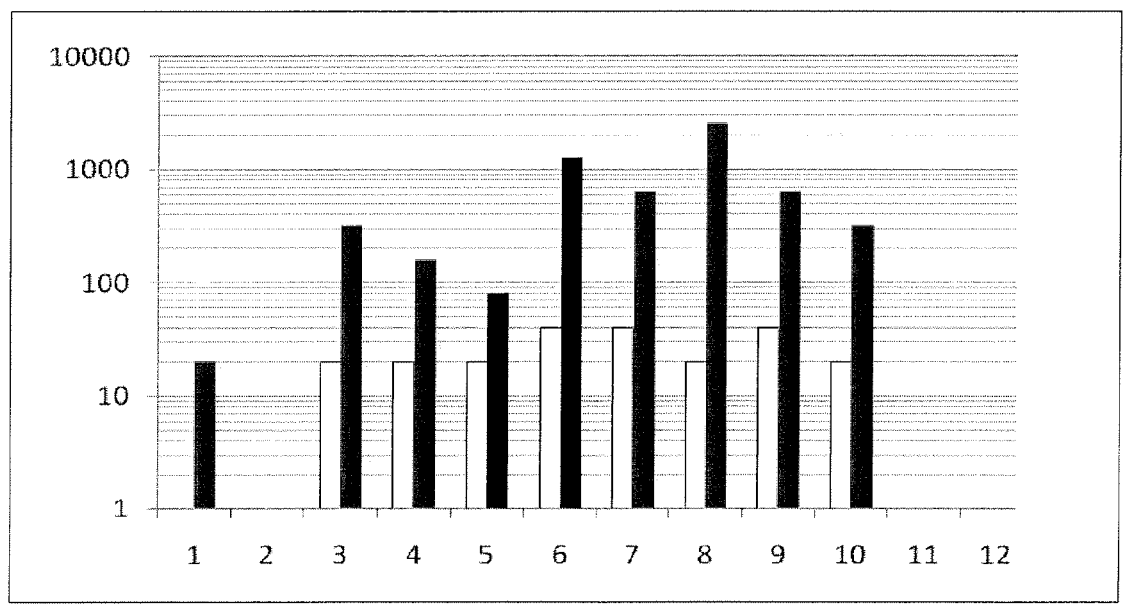

FIG. 5: In vivo evaluation of multi-epitope influenza virus-like particles.

Mice are immunized either with 50 ng (mice 1-5) or 100 ng (mice 6-10) purified VLP prepared from SEQ ID NO:3, and as control with PBS (mice 11-12). Antibody titers after prime injection (3 weeks post injection) are indicated as white boxes, titers after a boost injection are indicated as black boxes (6 weeks post injection). The titers are presented as dilution of mice sera (y-axis). VLPs effectively stimulate an antibody immune response. The best results are obtained when immunization is performed with 100 µl (mice 6-10), indicating a dose dependent immune response. A clear increase of the amount of anti-VLP antibodies is observed after boost. As expected, control animals (mice 11-12) showed no immune response.

Figure 6:
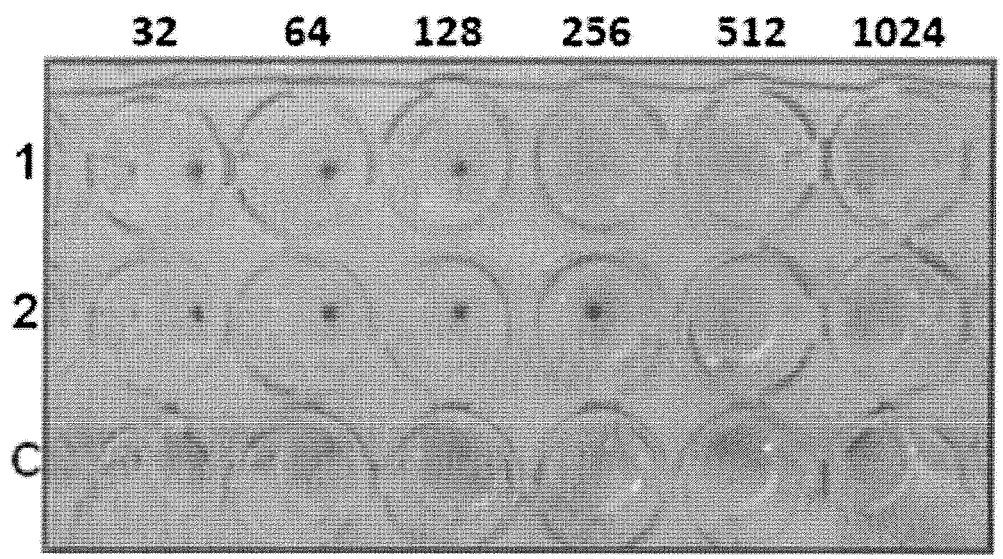

FIG. 6: Confirmation of specific immune response to multi-epitope influenza VLP by hemagglutination inhibition assay.

The ELISA test was performed with sera taken at week 6 post injection to analyze the presence of specific anti-HA antibodies. Multi-epitope virus-like particles prepared from SEQ ID NO:3 were coated onto a 96-well plate, mixed with the sera and incubated for 30 min. The sera were tested in a series of twofold dilutions (1:2 to 1:1024). After incubation erythrocytes were added and incubated for further 30 min. Specific anti-Influenza-HA antibodies from different mice binding to multi-epitope virus-like particles result in inhibition of erythrocyte agglutination up to a dilution 1:128 (1) and dilution 1:256 (2), visible as erythrocyte precipitation ("dot") in the middle of the well. No hemagglutination inhibition is observed with sera sample of the control mouse (C).

Figure 7:
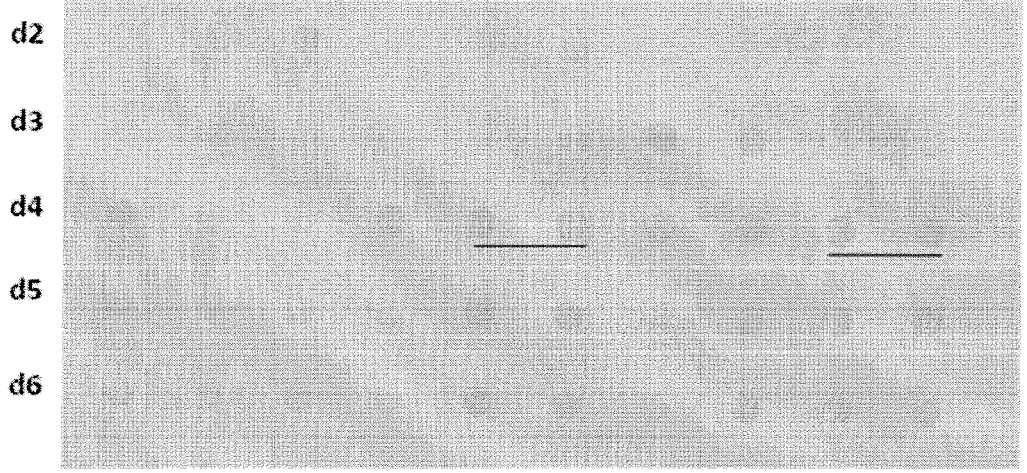
Figure 7:
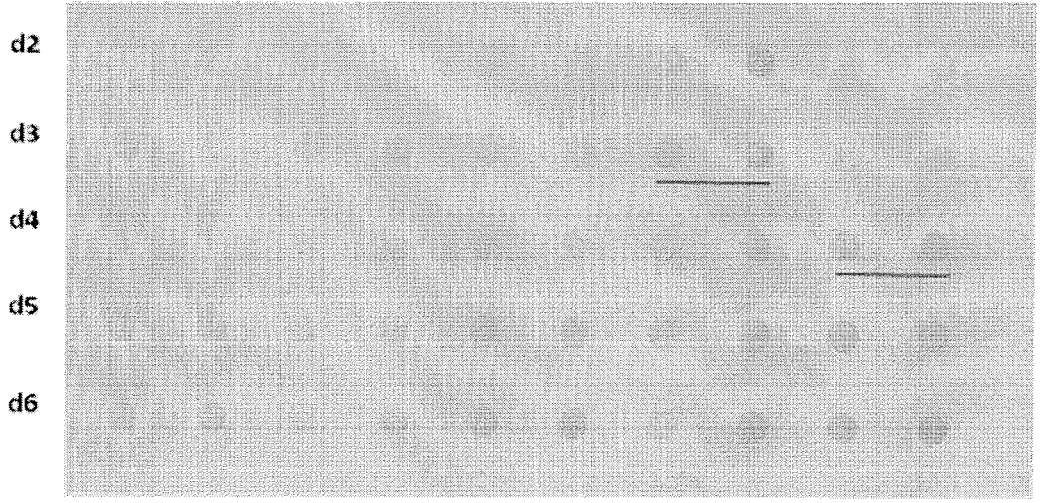

FIG. 7: Screening of best expression conditions using 50 mL bioreactors.

The initial cell amount in the range of $1\text{-}2 \times 10^6$ cells/mL (TOI, 1 or 2), virus inoculum (MOI, 0.01-2) and time of harvest (days post infection, d2-d6) were determined by dot blot analysis.

(A) Determination of best expression parameters of an expression construct carrying only one epitope L1 which is used as control. Detection by a specific anti-HPV18 antibody (Abcam).

(B) Determination of best expression parameters of a multi-epitope expression construct carrying two epitopes from different serotypes (SEQ ID NO:2). Detection by specific anti-HPV16-(Camvir, Santa Cruz) and anti-HPV18-(Abcam) antibodies against the two epitopes HPV16 L1 and HPV18 L1.

Figure 8A:
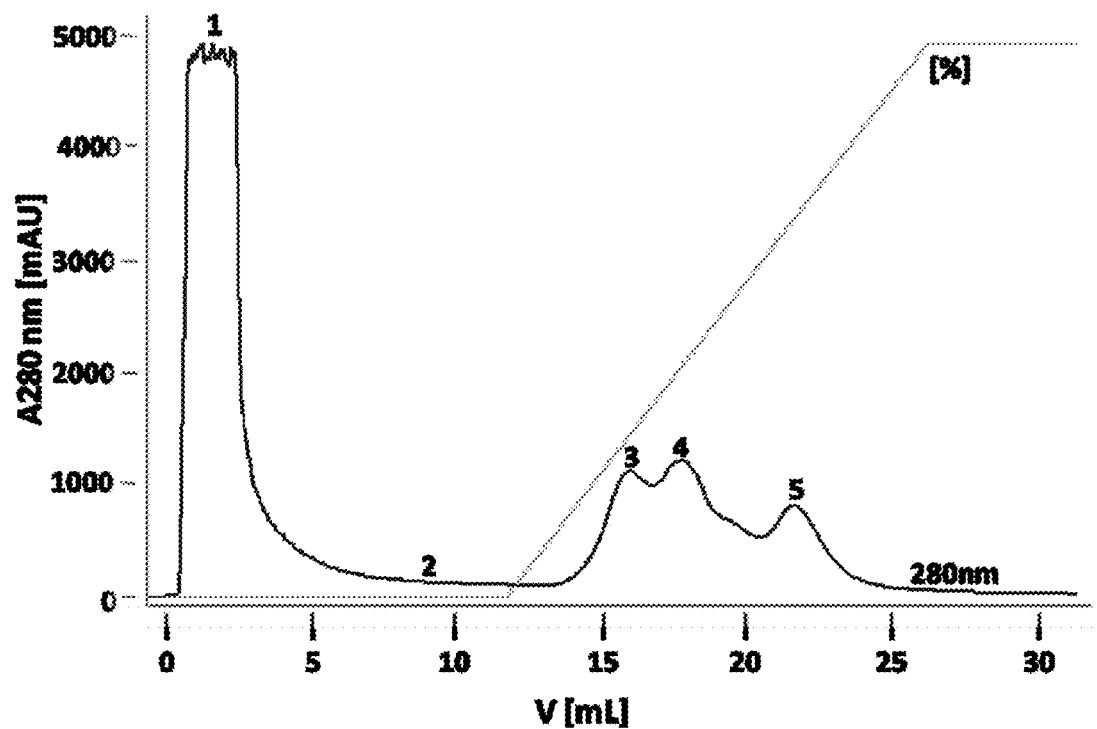
Figure 8B:
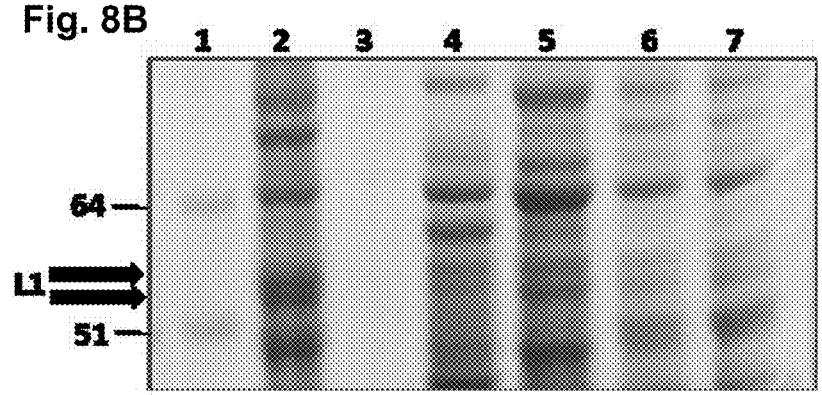

FIGS. 8A-8C: Chromatographic purification and analysis of multi-epitope human papilloma virus-like particles prepared from SEQ ID NO:2.

FIG. 8A Chromatogram of anion exchange chromatography using DEAE-sepharose column. Flow through (1), wash (2) and elution peaks (3-5) are indicated by numbers (1-5). The increased ionic strength of elution buffer is shown by a line [%]. 3=elution with 300 mM NaCl, 4=elution with 420 mM NaCl, 5=elution with 680 mM NaCl.

FIG. 8B Coomassie-stained SDS-PAGE. The presence of multiple epitopes of the virus-like particles were verified by analyzing different parts of the chromatogram. Lane1=ladder [kDa], lane 2=VLP before purification, lane 3=wash step, lane 4=elution with 300 mM NaCl, lane 5=elution with 420 mM NaCl, lane 6=elution with 500 mM NaCl, lane 7=elution with 680 mM NaCl. Epitopes are indicated by arrows (L1).

FIG. 8C Western blot analysis with coomassie-stained gel using specific antibodies against two epitopes which are indicated by arrows (L1).

DETAILED DESCRIPTION OF THE INVENTION

The invention aims at producing novel virus-like particles for use as vaccines, diagnostic tools and R&D tools based on recombinant DNA and cell cultivation techniques for production. Particles of the invention meet the demand for vaccines suitable to combat a potential pandemic influenza outbreak.

The recombinant virus-like particles of the invention are assembled by polypeptide chains that incorporate several, in particular two or more, such as two, three, four or five, or also multiples of three, such as six, nine or twelve, different epitopes or different proteins comprising epitopes which are selected either (a) from different viral strains of the same virus and/or (b) from different serotypes of the same virus and/or (c) from different viral strains specific for different hosts. These epitopes are then displayed on the particle surface. Selection of epitopes from different strains, serotypes and/or viruses specific for different hosts results in a multifunctional virus-like particle mimicking natural changes of viruses as they occur in nature, e.g. as observed in April 2009 during the outbreak of swine influenza. State of the art virus-like particles are either composed of a single protein or comprise up to three different epitopes derived from the same viral strain. The particle of the invention is encoded by a single DNA vector, either viral or plasmid based, which is used for the production in a host cell such as insect cells, bacterial cells and mammalian cells. In a preferred embodiment, the DNA vector is a baculovirus vector and the host cell an insect cell.

Epitopes of the invention are immunogenic peptides consisting of between 4 and 1000 amino acids, preferably between 6 and 100 amino acids, and are preferably neutralization epitopes. Neutralization epitopes are epitopes which, when bound by antibodies as the results of an immunogenic response, lead to neutralization of the virus carrying such a neutralizing epitope. Epitopes as understood herein may be repetitive, and may be part of a larger protein, in particular part of an antigen, part of a viral surface protein or part of a viral membrane protein. Such epitopes incorporated in viral surface proteins or viral membrane proteins are preferred. If the intended use of the virus-like particles according to the invention is as a R&D tool, diagnostics tool or a virus simulator it is important that the epitopes are part of complete viral proteins providing a complete virus-type surface.

Different viral strains of the invention are, for example, different strains of influenza virus, for example influenza virus A strains H1N1, H5N1, H9N1, H1N2, H2N2, H3N2 or H9N2, or also influenza virus B or influenza virus C.

Different serotypes of the invention are, for example, different serotypes of human papilloma virus (HPV), for example serotypes 6, 11, 16, 18, 31, 33, 35, 39, 45, 48, 52, 58 62, 66, 68, 70, 73 and 82, but also from the proto-oncogenic types HPV 5, 8, 14, 17, 20 and 47 or from papilloma relevant types HPV 6, 11, 13, 26, 28, 32 and 60.

Virus strains specific for different hosts means particularly adapted to the corresponding host, and are, for example, human influenza virus strains, swine influenza virus strains and avian influenza virus strains. In this context, specific for a host means that the virus is easily transmitted from one host to another host of the same type, but not to a different type of host. For example, an avian virus strain is easily transmitted from birds to other birds, but not to other animals or to humans.

In a preferred embodiment the particle comprising epitopes from different strains, serotypes and/or viruses specific for different hosts are combined with B- and/or T-cell epitopes in order to induce a broader immune response.

In another preferred embodiment the virus-like particle consists of proteins forming a complete virus-like surface, optionally further comprising capsid and nucleopore proteins.

The virus-like particle of the invention may further comprise fluorescent proteins, proteins useful for purification purposes of the particles or for attaching a label, and proteinaceous structures required for transport processes and stability.

The herein described polypeptides and virus like particles are generated in a shorter time and in unlimited amounts compared to actual vaccine manufacturing processes, due to the use of specific genetic and process engineering tools. The capability to assemble the required viral genes by modern molecular biology methods, such as the MultiBac technology (WO 2005/085456; I. Berger et al., Nature Biotechnology 22, 1583, 2004), Polybac technology (WO 2007/054250), or gene synthesis, for instance, allows for fast assembly of the coding DNA vector. The use of these technologies does not require any physical transfer of original, potentially dangerous viruses during the development, manufacturing or administration of virus-like particles and vaccines of the invention. For the construction of particles of the invention it is sufficient to use nucleotide sequences from an infected individual. This stands in major contrast to classical egg-based methods for generating vaccines, which require genetically modified virus as a seed-strain virus. Particles of the invention are manufactured using modern disposable tissue culture techniques which allow for high production capacity. In the preferred embodiment of baculoviral vector and insect cells as host cells the manufacturing process can be quickly set-up, and production times are short, i.e. in the range of weeks rather than months compared to egg-based methods. Additionally, the construction of disposable tissue culture facilities is less time-consuming and costly compared to setting up an egg-based facility. As a consequence large amounts of vaccine for a full population can be produced and re-produced within short time frames, and several different types of vaccines, e.g. seasonal influenza vaccines and pandemic influenza vaccines, can easily be produced in parallel. Difficult decisions by health authorities for the one or the other vaccine due to capacity limits of egg-based vaccine manufacturing plants will not be required.

The invention relates to a recombinant virus-like particle comprising two or more, such as two, three, four or five, or also multiples of three, such as six, nine or twelve, different epitopes or different proteins comprising epitopes which are selected either (a) from different viral strains of the same virus and/or (b) from different serotypes of the same virus and/or (c) from different viral strains specific for different hosts. Preferred are recombinant virus-like particle comprising three or more, preferably four or more different epitopes or different proteins comprising epitopes. Likewise preferred are recombinant virus-like particle comprising multiples of three, such as six, nine or twelve different epitopes or different proteins comprising epitopes. The epitopes are selected from two different strains, serotypes or virus strains specific for different hosts, or from three different strains, serotypes or virus strains specific for different hosts, or from four different strains or serotypes. Preferred are virus-like particles comprising several epitopes from three different strains or serotypes. Likewise preferred are virus-like particles comprising several epitopes from virus strains specific for two or three different hosts.

Furthermore the invention relates to a vector comprising two or more, such as two, three, four or five, or also multiples of three, such as six, nine or twelve, different polynucleotides coding for epitopes or for different proteins comprising epitopes which are selected either (a) from different viral strains of the same virus and/or (b) from different serotypes of the same virus and/or (c) from different viral strains specific for different hosts. "Polynucleotides" as used herein may represent a chain of between 12 and 3'000 nucleotides, includes oligonucleotides as commonly designated, and may be a viral gene or open reading frame from the mentioned different viral sources, in particular genes or open reading frames encoding viral surface proteins or viral membrane proteins.

Preferred are vectors coding for preferred virus-like particles mentioned hereinbefore.

Most preferred is a vector comprising a polynucleotide sequence selected from SEQ ID NO: 1 to 5.

In preferred embodiments a virus-like particle of the invention comprises (1) the same type of a surface protein from two or three different strains or serotypes of the same virus;

(2) a mixture of more than two different surface proteins from different viral strains, e.g. from influenza virus strains H5N1 and H1N1;

(3) a mixture of different surface proteins combined from viruses specific for different hosts, e.g. from influenza virus specific for swine, human and/or avian hosts.

Viruses considered as source for epitopes to be comprised in virus-like particles of the invention are, for example, influenza virus, HPV, HIV, CMV, Dengue, HCV and Newcastle Disease Virus. Epitopes may be derived from other viruses and from bacteria. Particularly preferred is influenza virus. Equally preferred is human papilloma virus (HPV).

Vectors considered are DNA vectors, and can either be a plasmid vector or a viral vector. Methods to assemble such vectors are standard methods of state of the art molecular biology. Preferred methods are MultiBac such as described in WO 2005/085456 and in I. Berger et al., Nature Biotechnology 22, 1583, 2004, or Polybac methods such as described in WO 2007/054250, combined with CAP™ technology and state of the art gene synthesis technologies. These technologies allow assembling a multi-gene co-expression DNA vector which is suitable for expression in different host cells. The preferred DNA vector of the invention is a baculoviral vector.

The host cell used for the expression of vectors of the invention can be any prokaryotic (e.g. *E. coli*) or eukaryotic expression cell line. For expression of a preferred baculoviral vector an insect cell line is preferred. Examples of insect cell lines are, e.g., SF9, SF21, Hi-5, Express Sf+, and S2 Schneider cells. For expression in a eukaryotic system, mammalian cells are preferred, in particular human cells, e.g. HeLa, Huh7, HEK293, HepG2, BHK, CHO, MT-2, bone-marrow fibroblasts, primary neural cells, or embryonic cells. For expression in yeast *S. cerevisiae, S. pombe, C. albicans*, or *P. pastoris* cells may be used.

Cultivation and propagation of host cells according to the invention can be done in any vessel, bioreactor or disposable unit providing the appropriate conditions for the particular host cell.

The virus-like particles of the invention can be used as vaccines. Furthermore they may be used as antigens in diagnostic tools, antigens for antibody generation, and as virus simulators for research and development tools, e.g. viral entry studies and virus-host interaction studies.

Vaccines according to the invention contain the recombinant virus-like particle in aqueous solution optionally further containing viscosity-regulating compounds, stabilizing compounds and/or adjuvants increasing the immunogenicity, as is known in the state of the art.

In a particular embodiment H3N2 Influenza virus-like particles are constructed using the methods of Berger et al., Nature Biotechnology, 2004, WO2005/085456 and WO 2007/054250 and CAP™ technology. At least one M1 and M2 gene of the H1N1 Influenza strain A/Puerto Rico/834 is cloned by PCR amplification into the transfer vector pFL (WO 2007/054250, FIG. 1) together with the HA gene of influenza A/Brisbane10/2007 and the NA gene of influenza A/Brisbane10/2007. The construct is confirmed by DNA sequencing.

In another particular embodiment the same cloning techniques are used to introduce at least one L1 gene of both serotypes HPV16 and HPV18 or further serotypes from the group 2, 4, 6, 11, 31, 33-35, 39, 40-45, 51-53, 55-59, 62, 66, 68, 70, 73, and 77, cloned into the transfer vector pFL (FIG. 1).

EXPERIMENTAL PART

The baculoviral vectors termed MultiBac or YFPMultiBac (WO 2005/085456), which allow propagation in *E. coli* cells, and CAP™ technology are used for generation of recombinant AcNPVs (*Autographa californica* nuclear polyhedrosis virus, a baculovirus) using a conventional system (Fitzgerald et al., Nature Methods, 3, 1021, 2006). 10 ng of the multigene vector is transformed in DH10MultiBac and/or DH10YFPMultiBac competent cells. Positive clones are selected by blue/white screening and PCR. The corresponding MultiBac bacmid DNA is isolated using the Birnboim & Doly method. Recombinant AcNPVs are generated by transfection of 1 μg of multi-gene MultiBac bacmid in $0.9\times10^6$ Sf21 (Invitrogen) cells using transfection reagent Fugene (Roche) according to the manufacturers protocol. Virus amplification is done as described previously (Fitzgerald et al., Nature Methods, 3, 1021, 2006). The titer of all recombinant AcNPVs is determined by plaque assay described in the Bac-to-Bac-Manual (Invitrogen). Protein production parameters like multiplicity of infection (MOI), cell number (TOI) and time of harvest (TOH) are analyzed with small scale expression studies.

Example 1

Generation of Expression Vector Construct

To manufacture various constructs the multiplication module M present in the transfer vector pFL (WO 2005/085456 and CAP™ technology) is used according to the described method in WO 2005/085456. DNA of epitopes are either obtained by isolation of viral RNA from original virus followed by reverse transcription combined with PCR (for the influenza virus epitopes) or by gene synthesis (provided by the company Geneart). The reverse transcription is performed using the RevertAid™ H Minus First strand cDNA Synthesis kit (Fermentas) according to the manufactures protocol. The cDNA (2 μL) is used as template for PCR reaction. The following conditions are used based on the manufacturer's protocol. For a 50 μL total volume reaction 0.2 mM dNTP (NEB), 1.2% DMSO, 0.5 μM reverse and forward primer (Microsynth), 10 μl 5× Phusion GC reaction buffer and 2U Phusion Hot Start Polymerase (Finnzyme) are used. For multigene assembly the appropriate restriction sites (BstZ17I, SpeI, PmeI, AvrII) are introduced using PCR. The PCR fragments are cut with the restriction enzymes followed by ligation and transformation processes to integrate the multiplication module into the transfer vector. The ligation is done over night at 4° C. using 500 ng linearized transfer vector (pFL), 4 μL PCR product and 1U T4-DNA-ligase (Fermentas). To generate the plasmid 4 μL ligation solution are added to 50 μl competent DH5α cells and incubated for 30 min on ice. After a heat shock at 42° C. for 30 sec and a 2 min cold shock at 4° C., 200 μl LB medium is added and incubated for 1 h at 37° C. and 220 rpm. Afterwards 80 μl of the cell suspension is plated on LB agar plates containing the appropriate antibiotics, in this case 100 μg ampicillin and 100 μg gentamycin. The whole procedure is repeated until all epitopes are introduced into the transfer vector.

Figure 1:
FIG. 1: Schematic representations of vector constructs expressing multiple-epitope virus-like particles.
(A) (SEQ ID NO:1) Multivalent influenza A virus simulator containing different epitopes (M1, M2) from H1N1 viral strains as well as H3N2 (HA, NA) viral strains
(B) (SEQ ID NO:2) Chimeric human papilloma virus-like particle containing an epitope (L1) from serotypes HPV16 and HPV18
Figure 1:
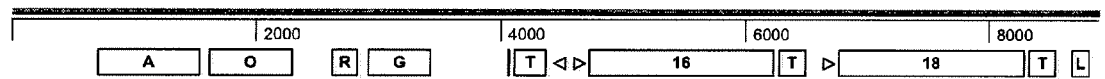
Figure 1:
Figure 1:
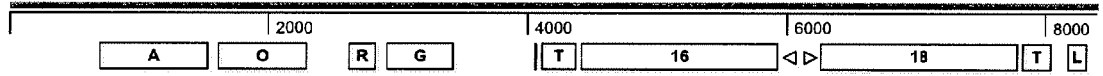
Figure 1:
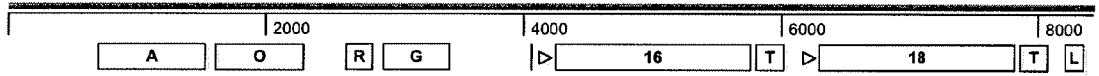

Influenza epitopes are selected from the genes HA and NA, both chosen from a H3N2/Brisbane10/2007 strain whereas epitopes from M1 and M2 are chosen from H1N1/Puerto Rico/834 strain. The M1 epitope is controlled by the promoter p10, all other epitopes are controlled by the polyhedrin promoter polh. All epitopes are present on the same vector construct (FIG. 1A, SEQ ID NO:1). Influenza B/Florida/2006 isolates are chosen to generate a construct with multiple epitopes from the genes HA, NA, M1 and M2 (FIG. 10, SEQ ID NO:3). Human papillomavirus epitopes are selected from the gene L1 from the cancer relevant serotypes HPV16 and HPV18 and are unified in one vector construct. Both epitopes are controlled by the polyhedrin promoter polh (FIG. 1B, SEQ ID NO:2). To improve the expression yield the p10 promoter is deleted in a further construct (FIG. 1E, SEC ID NO:5). In another construct HPV16 epitope is controlled by p10 promoter whereas the polyhedrin promoter polh is chosen for the HPV18 epitope (FIG. 1D, SEQ ID NO:4).

Example 2

Generation of Recombinant Baculovirus

This virus contains multiple epitopes to generate virus-like particles or virus simulators which present these epitopes on their surface. The virus-like particles can be used for different applications, e.g. as vaccines in the influenza field. The AcNPV-derived baculovirus contains multiple different epitopes from the viral strains recommended by WHO for the 2008/2009-VLP vaccination campaign. All genes of the transfer vector are transposed by site specific homologous recombination into MultiBac cells according to the protocol of WO 2005/085456.

10 ng transfer vector are added to 100 μl MultiBac competent cells and incubated for 30 min at 4° C. After a heat shock at 42° C. for 45 sec and a 2 min cold shock at 4° C. 400 μl LB medium is added and the cell solution is incubated for 4 h at 37° C. and 220 rpm. Different dilutions are plated on appropriate LB agar plates containing various antibiotic resistances. Based on blue/white and PCR screening several correct MultiBac clones are selected. The corresponding MultiBac bacmid DNA is isolated using the Birnboim & Doly method. At least four MultiBac bacmid clones are selected for initial transfection of insect cells like Sf9 or Sf21 to generate the recombinant AcNPV-derived baculovirus. This is generated by transfection of 1 μg of multi-gene MultiBac bacmid in $0.9 \times 10^6$ Sf21 (Invitrogen) cells using transfection reagent Fugene (Roche) according to the manufacturer's protocol. Virus amplification is done as described previously (Fitzgerald et al., Nature Methods, 3, 1021, 2006; Bac-to-Bac-Manual, Invitrogen). The virus is amplified to expand the volume and increase the infectious titer which is determined by plaque assay according to Bac-to-Bac-Manual (Invitrogen). The best expression construct is determined by 50 mL small scale expression experiments followed by determination of protein yield by Bradford Assay (ADV, Cytosceleton). Expression of best expressor is further verified by Western blot analysis with antibodies against the multiple different epitopes (FIG. 2A).

Example 3

Production and Purification of Multi-Epitope Influenza Virus-Like Particles in Insect Cells After determination of the best expression construct the biotechnological production parameters like cell line, cell amount (TOI), amount of recombinant virus inoculum (multiplicity of infection, MOD and time of harvest (TOH) are determined in 50 mL bioreactors. A matrix of different TOI, MOI and TOH are designed according to Eibl, Riesen and John (Bioforum 03/2009) and Friesen J. (Bachelor thesis, University of Applied Science, Esslingen, Germany). The expression of secreted or intracellular multi-epitope virus-like particles is observed for six to eight days with daily sample taking. For intracellular particles (e.g. HPV) the cell pellets are lysed with 50 mM TrisCl, pH 7.6, 100 mM NaCl, 0.1% TritonX100 and centrifuged for 10 min, at 4° C. and 8000×g. The epitopes of the virus-like particles present in the supernatant are further verified using a Dot-blot apparatus (Biometra) followed by Western blotting with specific antibodies. Conditions resulting in the highest yield are defined as expression parameters preferring a harvest time between three and four days. According to these defined parameters the virus-like particles are produced either in shaker flasks or wave cultibags in fall armyworm *Spodoptera frugiperda* cells Sf9 and Sf21. For multi-epitope influenza virus-like particles expression Sf21 cells are chosen with the following conditions: $1.5 \times 10^6$ cells/mL, MOI 0.05 and harvest time at day four post infection. Cells are propagated at 27° C. without carbon dioxide and fetal calf serum supplementation. According to defined time of harvest the secreted virus-like particles are collected by centrifugation at 500-1000×g for 20 min at 4° C. The supernatant volume containing the particles is reduced for purification by tangential flow filtration using cassettes (Sartocon-Slice 200, Sartorius and CentramateOS, PALL) with a cut-off of 100 kDa. The purification of virus-like particles is performed with scalable chromatographic methods and sucrose gradient ultracentrifugation.

The chromatographic purification is a multi-step purification using cation exchange, anion exchange and gel filtration chromatography. The supernatant is loaded onto a CaptoQ column connected to an FPLC-system (AEKTA purifier, GE Healthcare) in 50 mM phosphate buffer, pH 7.4. The particles are eluted with increasing salt concentrations in a linear gradient using 50 mM phosphate, 1 M NaCl, pH 7.4. The particle containing fractions are pooled and further purified by gel filtration chromatography (VLP from SEQ ID NO:1, FIG. 3). The purification is performed in 50 mM phosphate, 150 mM NaCl, pH 7.4 buffer using a HighLoad Superdex 200 pg column. All chromatography steps are analyzed by SDS-PAGE followed by coomassie staining and immunoblotting.

Example 4

Analysis of Purified Influenza Virus-Like Particles

To confirm the presence of the different epitopes purified material is analyzed by SDS-PAGE followed by coomassie staining or Western blot. 150 μl of different chromatography fractions are loaded on a 4-12% Bis-Tris NuPAGE gel (Invitrogen), run for 15 min at 150 V and for 45 min at 175 V and coomassie stained using SimplyBlueSafestain (Invitrogen). For immunoblotting the proteins are transferred onto a nitrocellulose membrane (BioRAD) at 19 V for 40 min using a semi-dry apparatus (BioRAD). After blocking unspecific binding sites for 30 min with 5% non-fat-dry-milk-TrisCl-Tween20 (0.1%) solution, the membrane is incubated over night at 4° C. with antibodies against HA, NA and matrix proteins. The membrane is washed several times with TrisCl-Tween20 (0.1%) buffer. Dependent on the source of primary antibody the second antibody is either an anti-mouse or anti-rabbit connected with alkaline phosphatase or horse-radish-peroxidase for detection. A co-localization of these proteins show the assembly and the production derived from one expression vector and one baculovirus (FIG. 3B, from SEQ ID NO:1). This co-localization can also be shown for the expression constructs containing the genes HA, NA and both matrix proteins M1 and M2 including their membrane anchors.

Example 5

Functionality of Influenza Virus-Like Particles (VLP)

To analyze if the VLPs correctly integrate the hemagglutinin protein (HA) in their surface, a standard hemagglutination assay using red blood cells (RBC) from chicken is performed (FIG. 4, VLP from SEQ ID NO:3). Twofold serial dilutions of the purified VLPs are carried out with PBS (1×) in V-formed 96 well plates. An equal amount of erythrocytes (1% solution) is added and incubated for 1 h at 4° C. The appearance of RBC aggregates on the bottom of the well indicates lack of hemagglutination. Titers are expressed as the inverse of the highest dilution of the purified VLP solution to agglutinate RBCs. The results obtained show that VLPs are able to agglutinate chicken erythrocytes and demonstrate indirectly the presence of HA on the VLP surface. The negative control (PBS) shows no agglutination.

Example 6

In Vivo Evaluation of Influenza VLP

The immunogenicity (stimulation of immune system) of VLPs (prepared from SEQ ID NO:3) is tested in vivo using two groups of mice which are subcutaneously immunized in a prime boost schedule at week 0 and week 3 respectively. Immunization is performed using 50 or 100 μl (50 or 100 ng) of VLPs in suspension. To determine the quality of the immune response of the VLPs alone, no adjuvant is used. Mice are bled at week 3 and 6 and sera are analyzed to look for antibody responses against the immunized VLPs. Results obtained show that VLPs are effective at stimulating an antibody immune response. The best results are obtained when immunization is performed with 100 μl, indicating a dose dependent immune response. A clear increase of the amount of anti-VLP antibodies is observed after boost. As expected, naïve animals show no immune response.

To reconfirm the specificity of the immune response, a hemagglutination inhibition test is performed at week 6 to analyze the presence of specific anti-HA antibodies. The results show that specific anti-Influenza-HA antibodies are able to inhibit erythrocyte agglutination up to a dilution 128 (mouse 6) and a dilution 256 (mouse 8). No hemagglutination inhibition is observed with sera sample of the naïve mouse. Newly generated multi-epitope influenza-VLPs are able to stimulate the immune system in a dose dependent manner. When the immune system is re-stimulated with a boost, the immune response increases at least 15 times. The specificity of the elicited immune response is analyzed by ELISA and a hemagglutination test.

Example 7

Production and Purification of Multi-Epitope Virus-Like Particles Carrying Human Papillomavirus Epitopes in Various Cell Lines The biotechnological production parameters like cell line, cell amount (TOI), amount of recombinant virus inoculum (multiplicity of infection, MOI) and time of harvest (TOH) are determined in 50 mL bioreactors (FIG. 7) according to Eibl et al. (Bioforum 3/2009). According to these defined parameters the virus-like particles are produced either in shaker flasks or wave cultibags in fall armyworm *Spodoptera frugiperda* cells Sf9 and Sf21. Multiple-epitope papilloma virus-like particles are expressed from SEQ ID NO:2 in Sf21 cells using $2\times10^6$ cells/mL, MOI 0.5 and harvest time at day three post infection. Cells are propagated at 27° C. without carbon dioxide and fetal calf serum supplementation. At defined harvest time (three days post infection) intracellular virus-like particles are collected by centrifugation at 500-1000×g for 20 min at 4° C. The cells are lysed using hypotonic phosphate buffers followed by ultrasonication. After a centrifugation step at 4° C. and 2000×g the supernatant was collected. The purification of virus-like particles is performed with scalable chromatographic methods and sucrose gradient ultra-centrifugation. The chromatographic purification is a multi-step purification using cation exchange, anion exchange and gel filtration chromatography. The supernatant is loaded onto a CaptoDEAE column connected to an FPLC-system (AEKTA purifier, GE Healthcare) in 50 mM phosphate buffer, pH 7.4. The particles are eluted with increasing salt concentrations in a linear gradient using 50 mM phosphate, 1 M NaCl, pH 7.4 (FIG. 8A). The particle containing fractions are pooled and further purified using a hydroxyapatite column. Binding is performed in 20 mM phosphate buffer, pH 7.0 followed by linear gradient elution with 500 mM phosphate, 150 mM NaCl, pH 7.0. To polish the multi-epitope particles a gel filtration chromatography is done. The purification is performed in 50 mM phosphate, 150 mM NaCl, pH 7.4 buffer using a HighLoad Superdex 200 pg column. All chromatography steps are analyzed by SDS-PAGE followed by coomassie staining and immunoblotting.

Example 8

Analysis of Purified Chimeric Human Papilloma Virus-Like Particles

To confirm the presence of the different epitopes in purified material, the VLP prepared from SEQ ID NO:2 is analyzed by SDS-PAGE followed by coomassie staining (FIG. 8B) and Western blot (FIG. 8C). For immunoblotting antibodies against L1 protein of different serotypes are used. 150 μl of different chromatography fractions are loaded on a 4-12% Bis-Tris NuPAGE gel (Invitrogen), run for 15 min at 150 V and a for 45 min at 175 V and coomassie stained using SimplyBlueSafestain (Invitrogen). For immunoblotting the proteins are transferred onto a nitrocellulose membrane (Bio-RAD) at 19 V for 40 min using a semi-dry apparatus (Bio-RAD). After blocking unspecific binding sites for 30 min with 5% non-fat-dry-milk-TrisCl-Tween20 (0.1%) solution, the membrane is incubated over night at 4° C. with antibodies against L1 epitopes. Camvir antibody (SantaCruz) is used for HPV16 and anti-HPV18ab (Abcam) for HPV18 detection. The membrane is washed several times with TrisCl-Tween20 (0.1%) buffer. The membrane is incubated for 1 h with an anti-mouse antibody connected with alkaline phosphatase for detection. The epitopes are detected by BCIP/NPT solution. A co-localization of these proteins show the assembly and production derived from one expression vector and one baculovirus.

Example 9

Functionality of Chimeric Human Papilloma Virus-like Particles (VLP)

To analyze if the human papilloma virus-like particles prepared from SEQ ID NO:2 correctly integrate the L1 protein in their surface, a standard ELISA assay is performed. Twofold serial dilutions of the purified VLPs are carried out with PBS (1×) in V-formed 96 well plates. An equal amount of a serotype specific antibody (concentration 1:1000) is added and incubated for 1 h at 37° C. Appropriate binding of the antibody to the L1 protein is detected using a second antibody with a horse-radish peroxidase and a chemoluminescent detection system. The results obtained show binding of antibodies to the recombinant expressed epitopes in a dose dependent manner. The negative control (PBS) showed no binding.

The invention claimed is:

1. A single baculoviral vector encoding a recombinant virus-like particle comprising two or more different surface proteins comprising epitopes, wherein the surface proteins are selected from (a) different viral strains of a same virus type, (b) different serotypes of a same virus type, or (c) different viral strains of a same virus type specific for different hosts; and wherein the baculoviral vector comprises a polynucleotide sequence selected from SEQ ID NOs:1 to 5.

2. The baculoviral vector according to claim 1, wherein said virus-like particle comprises three or more different epitopes or different proteins comprising epitopes.

3. The baculoviral vector according to claim 1, wherein said virus-like particle comprises four or more different epitopes or different proteins comprising epitopes.

4. The baculoviral vector according to claim 1, wherein said virus-like particle comprises six, nine or twelve different epitopes or different proteins comprising epitopes.

5. The baculoviral vector according to claim 1, wherein the epitopes are from three or more different virus strains or serotypes.

6. The baculoviral vector according to claim 1, wherein said virus-like particle further comprises B- and/or T-cell epitopes.

7. The baculoviral vector according to claim 1, wherein said virus-like particle further comprises proteins forming a complete virus-like surface and optionally capsid and/or nucleopore proteins.

8. The baculoviral vector according to claim 1, wherein said virus-like particle further comprises fluorescent proteins, proteins useful for purification purposes of the particles or for attaching a label.

9. The baculoviral vector according to claim 1, wherein the virus type is influenza virus.

10. The baculoviral vector according to claim 1, wherein the virus type is human papilloma virus.

11. An isolated host cell comprising a baculoviral vector according to claim 1.

* * * * *

SEQUENCE LISTING

```
<160> NUMBER OF SEQ ID NOS: 5

<210> SEQ ID NO 1
<211> LENGTH: 10482
<212> TYPE: DNA
<213> ORGANISM: Artificial
<220> FEATURE:
<223> OTHER INFORMATION: multi-epitope influenza A virus-like particle

<400> SEQUENCE: 1
ttctctgtca cagaatgaaa atttttctgt catctcttcg ttattaatgt ttgtaattga     60
ctgaatatca acgcttattt gcagcctgaa tggcgaatgg gacgcgccct gtagcggcgc    120
attaagcgcg gcgggtgtgg tggttacgcg cagcgtgacc gctacacttg ccagcgccct    180
agcgcccgct cctttcgctt tcttcccttc ctttctcgcc acgttcgccg gctttccccg    240
tcaagctcta aatcgggggc tccctttagg gttccgattt agtgctttac ggcacctcga    300
ccccaaaaaa cttgattagg gtgatggttc acgtagtggg ccatcgccct gatagacggt    360
ttttcgccct ttgacgttgg agtccacgtt cttaatagtg gactcttgtt ccaaactgga    420
acaacactca accctatctc ggtctattct tttgatttat aagggatttt gccgatttcg    480
gcctattggt taaaaaatga gctgatttaa caaaaattta acgcgaattt taacaaaata    540
ttaacgctta caatttaggt ggcacttttc ggggaaatgt gcgcggaacc cctatttgtt    600
tatttttcta aatacattca aatatgtatc cgctcatgag acaataaccc tgataaatgc    660
ttcaataata ttgaaaaagg aagagtatga gtattcaaca tttccgtgtc gcccttattc    720 cctttttgc ggcattttgc cttcctgttt ttgctcaccc agaaacgctg gtgaaagtaa    780
aagatgctga agatcagttg ggtgcacgag tgggttacat cgaactggat ctcaacagcg    840
gtaagatcct tgagagtttt cgccccgaag aacgttttcc aatgatgagc acttttaaag    900
ttctgctatg tggcgcggta ttatcccgta ttgacgccgg gcaagagcaa ctcggtcgcc    960
gcatacacta ttctcagaat gacttggttg agtactcacc agtcacagaa aagcatctta   1020
cggatggcat gacagtaaga gaattatgca gtgctgccat aaccatgagt gataacactg   1080
cggccaactt acttctgaca acgatcggag gaccgaagga gctaaccgct tttttgcaca   1140
acatggggga tcatgtaact cgccttgatc gttgggaacc ggagctgaat gaagccatac   1200
caaacgacga gcgtgacacc acgatgcctg tagcaatggc aacaacgttg cgcaaactat   1260
taactggcga actacttact ctagcttccc ggcaacaatt aatagactgg atggaggcgg   1320
ataaagttgc aggaccactt ctgcgctcgg cccttccggc tggctggttt attgctgata   1380
aatctggagc cggtgagcgt gggtctcgcg gtatcattgc agcactgggg ccagatggta   1440
agccctcccg tatcgtagtt atctacacga cggggagtca ggcaactatg gatgaacgaa   1500
atagacagat cgctgagata ggtgcctcac tgattaagca ttggtaactg tcagaccaag   1560
tttactcata tatactttag attgatttaa aacttcattt ttaatttaaa aggatctagg   1620
tgaagatcct ttttgataat ctcatgacca aaatccctta acgtgagttt tcgttccact   1680
gagcgtcaga ccccgtagaa aagatcaaag gatcttcttg agatcctttt tttctgcgcg   1740
taatctgctg cttgcaaaca aaaaaaccac cgctaccagc ggtggtttgt ttgccggatc   1800
```

```
aagagctacc aactcttttt ccgaaggtaa ctggcttcag cagagcgcag ataccaaata    1860
ctgttcttct agtgtagccg tagttaggcc accacttcaa gaactctgta gcaccgccta    1920
catacctcgc tctgctaatc ctgttaccag tggctgctgc cagtggcgat aagtcgtgtc    1980
ttaccgggtt ggactcaaga cgatagttac cggataaggc gcagcggtcg ggctgaacgg    2040
ggggttcgtg cacacagccc agcttggagc gaacgaccta caccgaactg agatacctac    2100
agcgtgagct atgagaaagc gccacgcttc ccgaagggag aaaggcggac aggtatccgg    2160
taagcggcag ggtcggaaca ggagagcgca cgagggagct tccaggggga aacgcctggt    2220
atctttatag tcctgtcggg tttcgccacc tctgacttga gcgtcgattt ttgtgatgct    2280
cgtcaggggg gcggagccta tggaaaaacg ccagcaacgc ggccttttta cggttcctgg    2340 cctttttgctg gccttttgct cacatgttct ttcctgcgtt atcccctgat tctgtggata    2400
accgtattac cgcctttgag tgagctgata ccgctcgccg cagccgaacg accgagcgca    2460
gcgagtcagt gagcgaggaa gcggaagagc gcctgatgcg gtattttctc cttacgcatc    2520
tgtgcggtat ttcacaccgc atagaccagc cgcgtaacct ggcaaaatcg gttacggttg    2580
agtaataaat ggatgccctg cgtaagcggg tgtgggcgga caataaagtc ttaaactgaa    2640
caaaatagat ctaaactatg acaataaagt cttaaactag acagaatagt tgtaaactga    2700
aatcagtcca gttatgctgt gaaaaagcat actggacttt tgttatggct aaagcaaact    2760
cttcattttc tgaagtgcaa attgcccgtc gtattaaaga gggcgtggc caagggcatg     2820 gtaaagacta tattcgcggc gttgtgacaa tttaccgaac aactccgcgg ccgggaagcc    2880
gatctcggct tgaacgaatt gttaggtggc ggtacttggg tcgatatcaa agtgcatcac    2940
ttcttcccgt atgcccaact ttgtatagag agccactgcg ggatcgtcac cgtaatctgc    3000
ttgcacgtag atcacataag caccaagcgc gttggcctca tgcttgagga gattgatgag    3060
cgcggtggca atgccctgcc tccggtgctc gccggagact gcgagatcat agatatagat    3120
ctcactacgc ggctgctcaa acttgggcag aacgtaagcc gcgagagcgc caacaaccgc    3180
ttcttggtcg aaggcagcaa gcgcgatgaa tgtcttacta cggagcaagt tcccgaggta    3240
atcggagtcc ggctgatgtt gggagtaggt ggctacgtct ccgaactcac gaccgaaaag    3300
atcaagagca gcccgcatgg atttgacttg gtcagggccg agcctacatg tgcgaatgat    3360
gcccatactt gagccaccta actttgtttt agggcgactg ccctgctgcg taacatcgtt    3420
gctgctgcgt aacatcgttg ctgctccata acatcaaaca tcgacccacg gcgtaacgcg    3480
cttgctgctt ggatgcccga ggcatagact gtacaaaaaa acagtcataa caagccatga    3540
aaaccgccac tgcgccgtta ccaccgctgc gttcggtcaa ggttctggac cagttgcgtg    3600
agcgcatacg ctacttgcat tacagtttac gaaccgaaca ggcttatgtc aactgggttc    3660
gtgccttcat ccgtttccac ggtgtgcgtc acccggcaac cttgggcagc agcgaagtcg    3720
aggcatttct gtcctggctg gcgaacgagc gcaaggtttc ggtctccacg catcgtcagg    3780
cattggcggc cttgctgttc ttctacggca aggtgctgtg cacggatctg cccttgcttc    3840
aggagatcgg tagacctcgg ccgtcgcggc gcttgccggt ggtgctgacc ccggatgaag    3900
tggttcgcat cctcggtttt ctggaaggcg agcatcgttt gttcgcccag gactctagct    3960
atagttctag tggttggcta cagctttgtt tgtactatca acaggttgaa ctgctgatca    4020
acagatcctc tacgcggccg cggtaccata acttcgtata gcatacatta tacgaagtta    4080
tctggtttaa acgtacccgt agtggctatg gcagggcttg ccgccccgac gttggctgcg    4140
agccctgggc cttcacccga acttgggggt tggggtgggg aaaaggaaga aacgcgggcg    4200
```

```
tattggtccc aatggggtct cggtggggta tcgacagagt gccagccctg ggaccgaacc    4260
ccgcgtttat gaacaaacga cccaacaccc gtgcgtttta ttctgtcttt ttattgccgt    4320
catagcgcgg gttccttccg gtattgtctc cttccgtgtt tcagttagcc tcccccatct    4380
cccggtaccg catgctatgc atgcggccgc tcacttgaac cgttgcatct gcaccccccat   4440 tcgtttctga taggcctgca aattttcaag aagatcattt ttcagaccag cactggagct    4500
aggatgagtc ccaatggttc tcatcgcttg caccatttgc ctagcctgac tagcaacctc    4560
catggcctct gctgcttgct cactcgatcc agccatttgc tccatagcct agctgtagt     4620 gctggctaaa accattctgt tctcatgtct gattagtgga ttggttgttg tcaccatttg    4680
cctatgagac cgatgctggg agtcagcaat ctgttcacag gttgcacata ccaggccaaa    4740
tgccacttca gtggtcacag cccccatcct gttgtatatg aggcccatac aactggcaag    4800
tgcaccagca gaataactga gtgagatttc tttggcccca tggaatgtta tctccctctt    4860
gagcttccta tacagtttaa ctgctttgtc catgttattt ggatcccgt tcccattaag     4920 ggcagtttgg acaaagcgtc tacgctgcag tcctcgctca ctgggcacgg tgagcgtgaa    4980
cacaaatcct aaaatcccct tagtcagagg tgacaggatt ggtcttgtct ttagccattc    5040
catgagaacc tcaagatcgg tgttcttccc tgcaaagaca tcttcaagtc tctgtgcgat    5100
ctcggctttg aggggcctg acgggatgat agagagaacg tacgtttcga cctcggttag     5160
aagactcatg gtggatccat cccgggtgat caagtcttcg tcgagtgatt gtaaataaaa    5220
tgtaatttac agtatagtat tttaattaat atacaaatga tttgataata attcttattt    5280
aactataata tattgtgttg ggttgaatta aaggtccgta tactagtatc gattcgcgac    5340
ctactccgga atattaatag atcatggaga taattaaaat gataaccatc tcgcaaataa    5400
ataagtattt tactgttttc gtaacagttt tgtaataaaa aaacctataa atattccgga    5460
ttattcatac cgtcccacca tcgggcgcgg atccaccatg aatccaaatc aaaagataat    5520
aacgattggc tctgtttctc tcaccatttc cacaatatgc ttcttcatgc aaattgccat    5580
cttgataact actgtaacat tgcatttcaa gcaatatgaa ttcaactccc ccccaaacaa    5640
ccaagtgatg ctgtgtgaac caacaataat agaaagaaac ataacagaga tagtgtatct    5700
gaccaacacc accatagaga aggaaatatg ccccaaacta gcagaataca gaaattggtc    5760
aaagccgcaa tgtgacatta caggatttgc accttttcct aaggacaatt cgattaggct    5820
ttccgctggt ggggacatct gggtgacaag agaaccttat gtgtcatgcg atcctgacaa    5880
gtgttatcaa tttgcccttg acagggaac aacactaaac aacgtgcatt caaatgcacc     5940
agtacgtgat aggacccctt atcggaccct attgatgaat gagttaggtg ttccttttca    6000
tctggggacc aagcaagtgt gcatagcatg gtccagctca agttgtcacg atggaaaagc    6060
atggctgcat gtttgtataa cggggatga taaaaatgca actgctagct tcatttacaa     6120
tgggaggctt gtagatagta ttgtttcatg gtccaaagaa atcctcagga cccaggagtc    6180
agaatgcgtt tgtatcaatg gaacttgtac agtagtaatg actgatggga gtgcttcagg    6240
aaaagctgat actaaaatac tattcattga ggagggaaa atcgttcata ctagcacatt    6300
gtcaggaagt gctcagcatg tcgaggagtg ctcctgctat cctcgatatc ctggtgtcag    6360
atgtgtctgc agagacaact ggaaaggctc aataggccc atcgtagata taaacataaa     6420
ggatcatagc actgttttcca gttatgtgtg ttcaggactt gttggagaca cacccagaaa    6480
aaacgacagc tccagcagta gccattgttt ggatcctaac aatgaagaag gtggtcatgg    6540
```

-continued

```
agtgaaaggc tgggcctttg atgatggaaa tgacgtgtgg atgggaagaa cgatcagcga   6600
gaagtcgcgc ttagggtatg aaaccttcaa agtcattgaa ggctggtcca accctaagtc   6660
caaattgcag ataaataggc aagtcatagt tgacagaggt aataggtccg gttattctgg   6720
tattttctct gttgaaggca aaagctgcat caatcggtgc ttttatgtgg agttgataag   6780
gggaagaaaa gaggaaactg aagtcttgtg gacctcaaac agtattgttg tgttttgtgg   6840
cacctcaggt acatatggaa caggctcatg gcctgatggg gcggacatca atctcatgcc   6900
tatataagta ctagaggatc ataatcagcc ataccacatt tgtagaggtt ttacttgctt   6960
taaaaaacct cccacacctc cccctgaacc tgaaacataa aatgaatgca attgttgttg   7020
ttaacttgtt tattgcagct tataatggtt acaaataaag caatagcatc acaaatttca   7080
caaataaagc attttttttca ctgcattcta gttgtggttt gtccaaactc atcaatgtat   7140
cttatcatgt ctggatctga tcactgcttg agcctagaag atccggctgc taacaaagcc   7200
cgaaaggaag ctgagttggc tgctgtggct agcttatcta gaaatattaa tagatcatgg   7260
agataattaa aatgataacc atctcgcaaa taaatagta ttttactgtt ttcgtaacag   7320
ttttgtaata aaaaaccta aaatattcc ggattattca taccgtccca ccatcgggcg   7380
caccatgagt cttctaaccg aggtcgaaac gcctatcaga aacgaatggg ggtgcagatg   7440
caacggttca agtgatcctc tcactattgc cgcaaatatc attgggatct gcacttgac   7500 attgtgatt cttgatcgtc ttttttttcaa atgcatttac cgtcgcttta aatacggact   7560
gaaaggaggg ccttctacgg aaggagtgcc aaagtctatg agggaagaat atcgaaagga   7620
acagcagagt gctgtggatg ctgacgatgg tcattttgtc agcatagagc tggagtaagt   7680
actagaggat cataatcagc cataccacat tgtagaggt tttacttgct ttaaaaaacc   7740
tcccacacct ccccctgaac ctgaaacata aaatgaatgc aattgttgtt gttaacttgt   7800
ttattgcagc ttataatggt tacaaataaa gcaatagcat cacaaattc acaaataaag   7860 catttttttc actgcattct agttgtggtt tgtccaaact catcaatgta tcttatcatg   7920
tctggatctg atcactgctt gagcctagaa gatccggctg ctaacaaagc ccgaaaggaa   7980
gctgagttgg ctgctgccac cgctgagcaa taactatcat aaccggaata ttaatagatc   8040
atggagataa ttaaaatgat aaccatctcg caaataaata agtatttac tgttttcgta   8100 acagttttgt aataaaaaaa cctataaata ttccggatta ttcataccgt cccaccatcg   8160
ggcgcggatc caccatgaag actatcattg ctttgagcta cattctatgt ctggttttca   8220
ctcaaaaact tcccggaaat gacaacagca cggcaacgct gtgccttggg caccatgcag   8280
taccaaacgg aacgatagtg aaaacaatca cgaatgacca aattgaagtt actaatgcta   8340
ctgagctggt tcagagttcc tcaacaggtg aaatatgcga cagtcctcat cagatccttg   8400
atggagaaaa ctgcacacta atagatgctc tattgggaga ccctcagtgt gatggcttcc   8460
aaaataagaa atgggacctt tttgttgaac gcagcaaagc ctacagcaac tgttaccctt   8520
atgatgtgcc ggattatgcc tcccttaggt cactagttgc ctcatccggc acactggagt   8580
ttaacaatga agcttcaat tggactggag tcactcaaaa cggaacaagc tctgcttgca   8640
taaggagatc taataacagt ttcttttagta gattgaattg gttgacccac ttaaaattca   8700
aatacccagc attgaacgtg actatgccaa acaatgaaaa atttgacaaa ttgtacattt   8760
ggggggttca ccacccgggt acggacaatg accaaatctt cccgtatgct caagcatcag   8820
gaagaatcac agtctctacc aaaagaagcc aacaaactgt aatcccgaat atcggatcta   8880
gacccagagt aaggaatatc cccagcagaa taagcatcta ttggacaata gtaaaaccgg   8940
```

| | |
|---|---|
| gagacatact tttgattaac agcacaggga atctaattgc tcctaggggt tacttcaaaa | 9000 |
| tacgaagtgg gaaaagctca ataatgagat cagatgcacc cattggcaaa tgcaattctg | 9060 |
| aatgcatcac tccaaacgga agcattccca atgacaaacc attccaaaat gtaaacagga | 9120 |
| tcacatacgg ggcctgtccc agatatgtta agcaaaacac tctgaaattg caacaggga | 9180 |
| tgcgaaatgt accagagaaa caaactagag gcatatttgg cgcaatcgcg ggtttcatag | 9240 |
| aaaatggttg ggagggaatg gtggatggtt ggtacggttt caggcatcaa aattctgagg | 9300 |
| gaataggaca agcagcagat ctcaaaagca ctcaagcagc aatcgatcaa atcaatggga | 9360 |
| agctgaatag gttgatcggg aaaaccaacg agaaattcca tcagattgaa aaagaattct | 9420 |
| cagaagtcga agggagaatt caggaccttg agaaatatgt tgaggacacc aaaatagatc | 9480 |
| tctggtcata caacgcggag cttcttgttg ccctggagaa ccaacataca attgatctaa | 9540 |
| ctgactcaga aatgaacaaa ctgtttgaaa aaacaaagaa gcaactgagg gaaaatgctg | 9600 |
| aggatatggg caatggttgt ttcaaaatat accacaaatg tgacaatgcc tgcataggat | 9660 |
| caatcagaaa tggaacttat gaccacgatg tatacagaga tgaagcatta aacaaccggt | 9720 |
| tccagatcaa gggcgttgag ctgaagtcag gatacaaaga ttggatccta tggatttcct | 9780 |
| ttgccatatc atgtttttg ctttgtgttg ctttgttggg gttcatcatg tgggcctgcc | 9840 |
| aaaaaggcaa cattaggtgc aacatttgca tttgagtact agaggatcat aatcagccat | 9900 |
| accacatttg tagaggtttt acttgcttta aaaaacctcc cacacctccc cctgaacctg | 9960 |
| aaacataaaa tgaatgcaat tgttgttgtt aacttgttta ttgcagctta taatggttac | 10020 |
| aaataaagca atagcatcac aaatttcaca aataaagcat tttttcact gcattctagt | 10080 |
| tgtggtttgt ccaaactcat caatgtatct tatcatgtct ggatctgatc actgcttgag | 10140 |
| cctagaagat ccggctgcta acaaagcccg aaggaagct gagttggctg ctgccaccgc | 10200 |
| tgagcaataa ctatcataac ccctaggaga tccgaaccag ataagtgaaa tctagttcca | 10260 |
| aactattttg tcattttaa ttttcgtatt agcttacgac gctacaccca gttcccatct | 10320 |
| attttgtcac tcttccctaa ataatcctta aaaactccat ttccacccct cccagttccc | 10380 |
| aactattttg tccgcccaca gcggggcatt tttcttcctg ttatgttttt aatcaaacat | 10440 |
| cctgccaact ccatgtgaca aaccgtcatc ttcggctact tt | 10482 |

<210> SEQ ID NO 2
<211> LENGTH: 8917
<212> TYPE: DNA
<213> ORGANISM: Artificial
<220> FEATURE:
<223> OTHER INFORMATION: multi-epitope human papilloma virus-like
      particle

<400> SEQUENCE: 2

| | |
|---|---|
| ttctctgtca cagaatgaaa attttttctgt catctcttcg ttattaatgt ttgtaattga | 60 |
| ctgaatatca acgcttattt gcagcctgaa tggcgaatgg gacgcgccct gtagcggcgc | 120 |
| attaagcgcg gcgggtgtgg tggttacgcg cagcgtgacc gctacacttg ccagcgccct | 180 |
| agcgcccgct cctttcgctt tcttcccttc ctttctcgcc acgttcgccg gctttccccg | 240 |
| tcaagctcta aatcgggggc tccctttagg gttccgattt agtgctttac ggcacctcga | 300 |
| ccccaaaaaa cttgattagg gtgatggttc acgtagtggg ccatcgccct gatagacggt | 360 |
| ttttcgccct ttgacgttgg agtccacgtt ctttaatagtg gactcttgtt ccaaactgga | 420 |
| acaacactca accctatctc ggtctattct tttgatttat aagggatttt gccgatttcg | 480 |

```
gcctattggt taaaaaatga gctgatttaa caaaaattta acgcgaattt taacaaaata      540
ttaacgctta caatttaggt ggcacttttc ggggaaatgt gcgcggaacc cctatttgtt      600 tattttcta aatacattca aatatgtatc cgctcatgag acaataaccc tgataaatgc       660
ttcaataata ttgaaaaagg aagagtatga gtattcaaca tttccgtgtc gcccttattc      720 cctttttgc ggcattttgc cttcctgttt ttgctcaccc agaaacgctg gtgaaagtaa       780
aagatgctga agatcagttg ggtgcacgag tgggttacat cgaactggat ctcaacagcg      840
gtaagatcct tgagagtttt cgccccgaag aacgttttcc aatgatgagc acttttaaag     900
ttctgctatg tggcgcggta ttatcccgta ttgacgccgg gcaagagcaa ctcggtcgcc      960
gcatacacta ttctcagaat gacttggttg agtactcacc agtcacagaa aagcatctta    1020
cggatggcat gacagtaaga gaattatgca gtgctgccat aaccatgagt gataacactg    1080
cggccaactt acttctgaca acgatcggag gaccgaagga gctaaccgct tttttgcaca    1140
acatggggga tcatgtaact cgccttgatc gttgggaacc ggagctgaat gaagccatac    1200
caaacgacga gcgtgacacc acgatgcctg tagcaatggc aacaacgttg cgcaaactat    1260
taactggcga actacttact ctagcttccc ggcaacaatt aatagactgg atggaggcgg    1320
ataaagttgc aggaccactt ctgcgctcgg cccttccggc tggctggttt attgctgata    1380
aatctggagc cggtgagcgt gggtctcgcg gtatcattgc agcactgggg ccagatggta    1440
agccctcccg tatcgtagtt atctacacga cggggagtca ggcaactatg gatgaacgaa    1500
atagacagat cgctgagata ggtgcctcac tgattaagca ttggtaactg tcagaccaag    1560
tttactcata tatactttag attgatttaa aacttcattt ttaatttaaa aggatctagg    1620
tgaagatcct ttttgataat ctcatgacca aaatccctta acgtgagttt tcgttccact    1680
gagcgtcaga ccccgtagaa aagatcaaag gatcttcttg agatcctttt tttctgcgcg    1740
taatctgctg cttgcaaaca aaaaaaccac cgctaccagc ggtggtttgt ttgccggatc    1800
aagagctacc aactcttttt ccgaaggtaa ctggcttcag cagagcgcag ataccaaata    1860
ctgttcttct agtgtagccg tagttaggcc accacttcaa gaactctgta gcaccgccta    1920
catacctcgc tctgctaatc ctgttaccag tggctgctgc cagtggcgat aagtcgtgtc    1980
ttaccgggtt ggactcaaga cgatagttac cggataaggc gcagcggtcg ggctgaacgg    2040
ggggttcgtg cacacagccc agcttggagc gaacgaccta ccgaactg agataccta     2100 agcgtgagct atgagaaagc gccacgcttc ccgaagggag aaaggcggac aggtatccgg    2160
taagcggcag ggtcggaaca ggagagcgca cgagggagc tccaggggga aacgcctggt    2220
atctttatag tcctgtcggg tttcgccacc tctgacttga gcgtcgattt ttgtgatgct    2280
cgtcaggggg gcggagccta tggaaaaacg ccagcaacgc ggccttttta cggttcctgg    2340
ccttttgctg gccttttgct cacatgttct ttcctgcgtt atcccctgat tctgtggata    2400
accgtattac cgcctttgag tgagctgata ccgctcgccg cagccgaacg accgagcgca    2460
gcgagtcagt gagcgaggaa gcggaagagc gcctgatgcg gtattttctc cttacgcatc    2520
tgtgcggtat ttcacaccgc atagaccagc cgcgtaacct ggcaaaatcg gttacggttg    2580
agtaataaat ggatgccctg cgtaagcggg tgtgggcgga caataaagtc ttaaactgaa    2640
caaaatagat ctaaactatg acaataaagt cttaaactag acagaatagt tgtaaactga    2700
aatcagtcca gttatgctgt gaaaaagcat actggacttt tgttatggct aaagcaaact    2760
cttcattttc tgaagtgcaa attgcccgtc gtattaaaga ggggcgtggc caagggcatg    2820
```

```
gtaaagacta tattcgcggc gttgtgacaa tttaccgaac aactccgcgg ccgggaagcc    2880
gatctcggct tgaacgaatt gttaggtggc ggtacttggg tcgatatcaa agtgcatcac    2940
ttcttcccgt atgcccaact ttgtatagag agccactgcg ggatcgtcac cgtaatctgc    3000
ttgcacgtag atcacataag caccaagcgc gttggcctca tgcttgagga gattgatgag    3060
cgcggtggca atgccctgcc tccggtgctc gccggagact gcgagatcat agatatagat    3120
ctcactacgc ggctgctcaa acttgggcag aacgtaagcc gcgagagcgc caacaaccgc    3180
ttcttggtcg aaggcagcaa gcgcgatgaa tgtcttacta cggagcaagt tcccgaggta    3240
atcggagtcc ggctgatgtt gggagtaggt ggctacgtct ccgaactcac gaccgaaaag    3300
atcaagagca gcccgcatgg atttgacttg gtcagggccg agcctacatg tgcgaatgat    3360
gcccatactt gagccaccta actttgtttt agggcgactg ccctgctgcg taacatcgtt    3420
gctgctgcgt aacatcgttg ctgctccata acatcaaaca tcgacccacg gcgtaacgcg    3480
cttgctgctt ggatgcccga ggcatagact gtacaaaaaa acagtcataa caagccatga    3540
aaaccgccac tgcgccgtta ccaccgctgc gttcggtcaa ggttctggac cagttgcgtg    3600
agcgcatacg ctacttgcat tacagtttac gaaccgaaca ggcttatgtc aactgggttc    3660
gtgccttcat ccgtttccac ggtgtgcgtc acccggcaac cttgggcagc agcgaagtcg    3720
aggcatttct gtcctggctg gcgaacgagc gcaaggtttc ggtctccacg catcgtcagg    3780
cattggcggc cttgctgttc ttctacggca aggtgctgtg cacggatctg cccttgcttc    3840
aggagatcgg tagacctcgg ccgtcgcggc gcttgccggt ggtgctgacc ccggatgaag    3900
tggttcgcat cctcggtttt ctggaaggcg agcatcgttt gttcgcccag gactctagct    3960
atagttctag tggttggcta cagctttgtt tgtactatca acaggttgaa ctgctgatca    4020
acagatcctc tacgcggccg cggtaccata acttcgtata gcatacatta tacgaagtta    4080
tctggtttaa acgtacccgt agtggctatg cagggcttgc cgcccccgac gttggctgcg    4140
agccctgggc cttcacccga acttgggggt tggggtgggg aaaaggaaga aacgcgggcg    4200
tattggtccc aatggggtct cggtggggta tcgacagagt gccagccctg ggaccgaacc    4260
ccgcgtttat gaacaaacga cccaacaccc gtgcgtttta ttctgtcttt ttattgccgt    4320
catagcgcgg gttccttccg gtattgtctc cttccgtgtt tcagttagcc tcccccatct    4380
cccggtaccg catgctatgc atatcccggg tgatcaagtc ttcgtcgagt gattgtaaat    4440
aaaatgtaat ttacagtata gtattttaat taatatacaa atgatttgat aataattctt    4500
atttaactat aatatattgt gttgggttga attaaaggtc cgtatactag tatcgattcg    4560
cgacctactc cggaatatta atagatcatg gagataatta aaatgataac catctcgcaa    4620
ataaataagt attttactgt tttcgtaaca gttttgtaat aaaaaaacct ataaatattc    4680
cggattattc ataccgtccc accatcgggc gcggatccgc caccatgtcc ctgtggctgc    4740
cctccgaggc taccgtgtac ctgcccccg tgccccgtgtc caaggtggtg tccaccgacg    4800
agtacgtggc tcgtaccaac atctactacc acgctgcac ctcccgtctg ctggctgtgg    4860
gtcaccccta cttccccatc aagaagccca acaacaacaa gatcctggtg cccaaggtgt    4920
ccggcctgca gtaccgtgtg ttccgtatcc acctgcccga ccccaacaag ttcggtttcc    4980
ccgacacctc cttctacaac cctgacaccc agcgcctcgt gtgggcttgc gtgggcgtgg    5040
aggtcggccg tggccagccc ctgggtgtcg gtatctccgg tcaccccctg ctgaacaagc    5100
tggacgacac cgagaacgct tccgcttacg ctgctaacgc tggtgtcgac aaccgcgagt    5160
gcatctccat ggactacaag cagacccagc tgtgcctgat cggttgcaag cccccccatcg    5220
```

```
gcgagcactg gggcaagggt tccccctgca ccaacgtggc tgtgaacccc ggcgactgcc    5280
cccctctcga gctgatcaac accgtgatcc aggacggcga catggtggac accggtttcg    5340
gtgctatgga cttcaccacc ctgcaggcta acaagtccga ggtgcccctg acatctgca     5400
cctccatctg caagtacccc gactacatca agatggtgtc cgagccctac ggcgactccc    5460
tgttcttcta cctgcgtcgt gagcagatgt tcgtgcgtca cctgttcaac cgtgctggtg    5520
ctgtgggcga aacgtgccc gacgacctgt acatcaaggg ttccggttcc accgctaacc     5580
tggcttccag caactacttc cctacccct ccggttccat ggtcacctcc gacgctcaga     5640
tcttcaacaa gccctactgg ctgcagcgtg ctcagggtca caacaacggt atctgctggg    5700
gcaaccagct gttcgtgacc gtggtcgaca ccacccgttc caccaacatg tctctgtgcg    5760
ctgctatctc cacctccgag actacctaca agaacaccaa cttcaaggag tacctgcgtc    5820
acggcgagga gtacgacctg cagttcatct tccagctgtg caagatcacc ctgaccgctg    5880
acgtgatgac ctacatccac tccatgaact ccactatcct cgaagattgg aacttcggtc    5940
tgcagccccc tcccggtggc accctcgagg acacctaccg tttcgtcacc tcccaggcta    6000
tcgcttgcca gaagcacacc ccccctgctc ccaaggagga ccccctgaag aagtacacct    6060
tctgggaggt caacctgaag gagaagttct ccgctgacct ggaccagttc cccctgggtc    6120
gcaagttcct gctgcaggcc ggactgaagg ccaagcccaa gttcaccctg gcaagcgca     6180
aggctacccc caccaccctcc tccacctcca ccaccgctaa gaggaagaag cgcaagctgt    6240
aaaagcttgt cgagaagtac tagaggatca taatcagcca taccacattt gtagaggttt    6300
tacttgcttt aaaaaacctc ccacacctcc ccctgaacct gaaacataaa atgaatgcaa    6360
ttgttgttgt taacttgttt attgcagctt ataatggtta caaataaagc aatagcatca    6420
caaattcac aaataaagca tttttttcac tgcattctag ttgtggtttg tccaaactca    6480
tcaatgtatc ttatcatgtc tggatctgat cactgcttga gcctagaaga tccggctgct    6540
aacaaagccc gaaaggaagc tgagttggct gctgtggcta gctttgttta actttaagaa    6600
ggagatacat ctagaaatat taatagatca tggagataat taaatgata accatctcgc     6660
aaataaataa gtattttact gttttcgtaa cagttttgta ataaaaaaac ctataaatat    6720
tccggattat tcataccgtc ccaccatcgg gcgcggatcc gccaccatgg ctctgtggcg    6780
tccctccgac aacaccgtgt acctgccccc tccctccgtg ctcgtgtgg tcaacaccga    6840
cgactacgtg acccgtacct ccatcttcta ccacgctggt tcctcccgtc tgctgaccgt    6900
gggcaaccc tacttccgtg tgcccgctgg cgtggcaac aagcaggaca tccccaaggt     6960
gtccgcttac cagtaccgtg tgttccgtgt gcagctgccc gaccccaaca gttcggtct     7020
gcccgacacc tccatctaca accccgagac tcagcgcctc gtgtgggctt gcgctggtgt    7080
cgagatcggt cgtggccagc cctgggtgt cggcctgtcc ggtcaccct tctacaacaa     7140
gctggacgac accgagtcct cccacgctgc tacctccaac gtgtccgagg acgtgcgcga    7200
caacgtgtct gtggactaca agcagaccca gctgtgcatc ctgggttgcg ctcccgctat    7260
cggcgagcac tgggctaagg gcaccgcttg caagtcccgt cctctgtccc agggcgactg    7320
ccccccctctc gagctgaaga acaccgtgct cgaggacggc gacatggtgg acaccggtta    7380
cggtgctatg gacttcagca ccctgcagga caccaagtgc gaggtgcccc tggacatctg    7440
ccagtccatc tgcaagtacc ccgactacct gcagatgtcc gctgaccct acggcgactc    7500
tatgttcttc tgcctgcgtc gtgagcagct gttcgctcgt cacttctgga accgtgctgg    7560
```

```
caccatgggt gacaccgtgc cccagtccct gtacatcaag ggcaccggca tgcgtgcttc    7620
ccccggttcc tgcgtgtact cccttcccc  ctccggttcc atcgtgacct ccgactccca    7680
gctgttcaac aagccctact ggctgcacaa ggctcagggt cacaacaacg tgtctgctg     7740
gcacaaccag ctgttcgtga ccgtggtcga caccacccgt tccaccaacc tgaccatctg    7800
cgcttccacc cagtccccg  tgcccggcca gtacgacgct accaagttca gcagtactc     7860
ccgtcacgtg gaggagtacg acctgcagtt catcttccag ctctgcacta tcaccctgac    7920
cgctgacgtg atgtcctaca tccactccat gaactcctct atcctcgaag attggaactt    7980
cggtgtcccc cctccccca  ctacctccct ggtggacact taccgtttcg tgcagtccgt    8040
ggctatcacc tgccagaagg acgctgctcc cgctgagaac aaggacccct acgacaagct    8100
gaagttctgg aacgtggacc tgaaggagaa gttctccctg gacctggacc agtacccct     8160
gggtcgcaag ttcctggtgc aggctggcct gaggcgcaag cccaccatcg gtccccgcaa    8220
gcgttccgct ccctccgcta ccacctcctc caagcccgcc aagcgtgtgc gtgtgcgcgc    8280
tcgcaagtaa gctagcaagc ttgtcgagaa gtactagagg atcataatca gccataccac    8340
atttgtagag gttttacttg ctttaaaaaa cctcccacac ctccccctga acctgaaaca    8400
taaaatgaat gcaattgttg ttgttaactt gtttattgca gcttataatg gttacaaata    8460
aagcaatagc atcacaaatt tcacaaataa agcattttt  tcactgcatt ctagttgtgg    8520
tttgtccaaa ctcatcaatg tatcttatca tgtctggatc tgatcactgc ttgagcctag    8580
aagatccggc tgctaacaaa gcccgaaagg aagctgagtt ggctgctgcc accgctgagc    8640
aataactatc ataccccta  ggagatccga accagataag tgaaatctag ttccaaacta    8700
ttttgtcatt tttaatttc  gtattagctt acgacgctac acccagttcc catctattt     8760
gtcactcttc cctaaataat ccttaaaaac tccatttcca cccctcccag ttcccaacta    8820
ttttgtccgc ccacagcggg gcatttttct tcctgttatg tttttaatca aacatcctgc    8880
caactccatg tgacaaaccg tcatcttcgg ctacttt                             8917
```

<210> SEQ ID NO 3
<211> LENGTH: 10595
<212> TYPE: DNA
<213> ORGANISM: Artificial
<220> FEATURE:
<223> OTHER INFORMATION: multi-epitope influenza B virus-like particle

<400> SEQUENCE: 3

```
ttctctgtca cagaatgaaa attttttctgt catctcttcg ttattaatgt ttgtaattga     60
ctgaatatca acgcttattt gcagcctgaa tggcgaatgg gacgcgccct gtagcggcgc    120
attaagcgcg gcgggtgtgg tggttacgcg cagcgtgacc gctacacttg ccagcgccct    180
agcgcccgct cctttcgctt tcttcccttc ctttctcgcc acgttcgccg gctttccccg    240
tcaagctcta aatcgggggc tccctttagg gttccgattt agtgctttac ggcacctcga    300
ccccaaaaaa cttgattagg gtgatggttc acgtagtggg ccatcgccct gatagacggt    360
ttttcgccct ttgacgttgg agtccacgtt cttaatagtg gactcttgtt ccaaactgga    420
acaacactca accctatctc ggtctattct tttgatttat aagggatttt gccgatttcg    480
gcctattggt taaaaaatga gctgatttaa caaaaattta acgcgaattt taacaaaata    540
ttaacgctta caatttaggt ggcactttt  ggggaaatgt gcgcggaacc cctatttgtt    600
tatttttcta aatacattca aatatgtatc cgctcatgag acaataaccc tgataaatgc    660
ttcaataata ttgaaaaagg aagagtatga gtattcaaca tttccgtgtc gcccttattc    720
```

```
ccttttttgc ggcattttgc cttcctgttt ttgctcaccc agaaacgctg gtgaaagtaa      780
aagatgctga agatcagttg ggtgcacgag tgggttacat cgaactggat ctcaacagcg      840
gtaagatcct tgagagtttt cgccccgaag aacgttttcc aatgatgagc acttttaaag      900
ttctgctatg tggcgcggta ttatcccgta ttgacgccgg gcaagagcaa ctcggtcgcc      960
gcatacacta ttctcagaat gacttggttg agtactcacc agtcacagaa aagcatctta     1020
cggatggcat gacagtaaga gaattatgca gtgctgccat aaccatgagt gataacactg     1080
cggccaactt acttctgaca acgatcggag gaccgaagga gctaaccgct ttttgcaca      1140 acatggggga tcatgtaact cgccttgatc gttgggaacc ggagctgaat gaagccatac     1200
caaacgacga gcgtgacacc acgatgcctg tagcaatggc aacaacgttg cgcaaactat     1260
taactggcga actacttact ctagcttccc ggcaacaatt aatagactgg atggaggcgg     1320
ataaagttgc aggaccactt ctgcgctcgg cccttccggc tggctggttt attgctgata     1380
aatctggagc cggtgagcgt gggtctcgcg gtatcattgc agcactgggg ccagatggta     1440
agccctcccg tatcgtagtt atctacacga cggggagtca ggcaactatg gatgaacgaa     1500
atagacagat cgctgagata ggtgcctcac tgattaagca ttggtaactg tcagaccaag     1560
tttactcata tactttag attgatttaa aacttcattt ttaatttaaa aggatctagg       1620
tgaagatcct tttgataat ctcatgacca aaatccctta acgtgagttt tcgttccact      1680
gagcgtcaga cccgtagaa aagatcaaag gatcttcttg agatcctttt tttctgcgcg     1740
taatctgctg cttgcaaaca aaaaaaccac cgctaccagc ggtggtttgt ttgccggatc     1800
aagagctacc aactctttt ccgaaggtaa ctggcttcag cagagcgcag ataccaaata    1860
ctgttcttct agtgtagccg tagttaggcc accacttcaa gaactctgta gcaccgccta    1920
catacctcgc tctgctaatc ctgttaccag tggctgctgc cagtggcgat aagtcgtgtc    1980
ttaccgggtt ggactcaaga cgatagttac cggataaggc gcagcggtcg ggctgaacgg    2040
ggggttcgtg cacacagccc agcttggagc gaacgaccta caccgaactg agatacctac    2100
agcgtgagct atgagaaagc gccacgcttc ccgaagggag aaaggcggac aggtatccgg    2160
taagcggcag ggtcggaaca ggagagcgca cgagggagct tccaggggga aacgcctggt    2220
atctttatag tcctgtcggg tttcgccacc tctgacttga gcgtcgattt ttgtgatgct    2280
cgtcaggggg gcggagccta tggaaaaacg ccagcaacgc ggccttttta cggttcctgg    2340
ccttttgctg gccttttgct cacatgttct ttcctgcgtt atcccctgat tctgtggata    2400
accgtattac cgcctttgag tgagctgata ccgctcgccg cagccgaacg accgagcgca    2460
gcgagtcagt gagcgaggaa gcggaagagc gcctgatgcg gtattttctc cttacgcatc    2520
tgtgcggtat ttcacaccgc atagaccagc cgcgtaacct ggcaaaatcg gttacggttg    2580
agtaataaat ggatgccctg cgtaagcggg tgtgggcgga caataaagtc ttaaactgaa    2640
caaaatagat ctaaactatg acaataaagt cttaaactag acagaatagt tgtaaactga    2700
aatcagtcca gttatgctgt gaaaaagcat actggacttt tgttatggct aaagcaaact    2760
cttcattttc tgaagtgcaa attgcccgtc gtattaaaga ggggcgtggc caagggcatg    2820
gtaaagacta tattcgcggc gttgtgacaa tttaccgaac aactccgcgg ccgggaagcc    2880
gatctcggct tgaacgaatt gttaggtggc ggtacttggg tcgatatcaa agtgcatcac    2940
ttcttcccgt atgcccaact ttgtatagag agccactgcg gatcgtcac cgtaatctgc     3000 ttgcacgtag atcacataag caccaagcgc gttggcctca tgcttgagga gattgatgag    3060
```

```
cgcggtggca atgccctgcc tccggtgctc gccggagact gcgagatcat agatatagat   3120
ctcactacgc ggctgctcaa acttgggcag aacgtaagcc gcgagagcgc caacaaccgc   3180
ttcttggtcg aaggcagcaa gcgcgatgaa tgtcttacta cggagcaagt tcccgaggta   3240
atcggagtcc ggctgatgtt gggagtaggt ggctacgtct ccgaactcac gaccgaaaag   3300
atcaagagca gcccgcatgg atttgacttg gtcagggccg agcctacatg tgcgaatgat   3360
gcccatactt gagccaccta actttgtttt agggcgactg ccctgctgcg taacatcgtt   3420
gctgctgcgt aacatcgttg ctgctccata acatcaaaca tcgacccacg gcgtaacgcg   3480
cttgctgctt ggatgcccga ggcatagact gtacaaaaaa acagtcataa caagccatga   3540
aaaccgccac tgcgccgtta ccaccgctgc gttcggtcaa ggttctggac cagttgcgtg   3600
agcgcatacg ctacttgcat tacagtttac gaaccgaaca ggcttatgtc aactgggttc   3660
gtgccttcat ccgtttccac ggtgtgcgtc acccggcaac cttgggcagc agcgaagtcg   3720
aggcatttct gtcctggctg gcgaacgagc gcaaggtttc ggtctccacg catcgtcagg   3780
cattggcggc cttgctgttc ttctacggca aggtgctgtg cacggatctg cccttgcttc   3840
aggagatcgg tagacctcgg ccgtcgcggc gcttgccggt ggtgctgacc ccggatgaag   3900
tggttcgcat cctcggtttt ctggaaggcg agcatcgttt gttcgcccag gactctagct   3960
atagttctag tggttggcta cagctttgtt tgtactatca acaggttgaa ctgctgatca   4020
acagatcctc tacgcggccg cggtaccata acttcgtata gcatacatta tacgaagtta   4080
tctggtttaa acgtacccgt agtggctatg gcagggcttg ccgccccgac gttggctgcg   4140
agccctgggc cttcacccga acttgggggt tggggtgggg aaaaggaaga aacgcgggcg   4200
tattggtccc aatggggtct cggtggggta tcgacagagt gccagccctg ggaccgaacc   4260
ccgcgtttat gaacaaacga cccaacaccc gtgcgtttta ttctgtcttt ttattgccgt   4320
catagcgcgg gttccttccg gtattgtctc cttccgtgtt tcagttagcc tcccccatct   4380
cccggtacct tataagtatt tcctcacaag agctgaattt cccatagagc tctgttttag   4440
cacttccatt acatctttgg caattccttc tccattcttt tgacttgctc ctagagatct   4500
caacactcca atgttgtttt gcagctcttc tgctagtttt tggacgtctt ctcccttttcc  4560
cattccattc attgtctttg ctgtgttcat agctgaaacc atctgcattt ctcgtcttac   4620
tccaggtacc gaagaccttg ctgctctgct atgggctcta tgcgagtgcg atgcttgttt   4680
ctcgcataaa gcacagagcg ttcctagttt tacttgcatt gaatagtttt cagggtttag   4740
gtacatgacc ataagacaat atagtaatgc tgagcttttcg tggccttctg ctatttcaaa   4800
tgcttcatga aagcttacac atcttctcat ttttctctca gctagaatta ggcctttctt   4860
ctttgttgct gttgttccca ttcctgacag gggctctgtg atgaatctcc tttttctttc   4920
ttggtctttg ggttttaaaa agcatataga ggcaccaatt agtgcttttt gtatatcagt   4980
taggcacctt tgttttttta tccattccaa agcagaatct aggtcaaatt ctttcccacc   5040
gaaccaacag tgtaattttt cagctagttc tgctttgcct tctccatctt ctattagtga   5100
aagcaggtag gcaattgtgt ctccaaacag cgacatggtg gcatcccggg tgatcaagtc   5160
ttcgtcgagt gattgtaaat aaaatgtaat ttacagtata gtattttaat taatatacaa   5220
atgatttgat aataattctt atttaactat aatatattgt gttgggttga attaaaggtc   5280
cgtatactag tatcgattcg cgacctactc cggaatatta atagatcatg gagataatta   5340
aaatgataac catctcgcaa ataaataagt attttactgt tttcgtaaca gttttgtaat   5400
aaaaaaacct ataaatattc cggattattc ataccgtccc accatcgggc gcggatccac   5460
```

```
catgaaggca ataattgtac tactcatggt agtaacatcc aatgcagatc gaatctgcac   5520
tggaataaca tcttcaaact cacctcatgt ggtcaaaaca gccactcaag gggaggtcaa   5580
tgtgactggt gtgataccac taacaacaac accaacaaaa tcttattttg caaatctcaa   5640
aggaacaagg accagaggga aactatgccc agactgtctc aactgcacag atctggatgt   5700
ggctttgggc agaccaatgt gtgtgggdac cacaccttcg gcgaaagctt caatactcca   5760
cgaagtcaaa cctgttacat ccgggtgctt tcctataatg cacgcacagaa caaaaatcag   5820 gcaactaccc aatcttctca gaggatatga aaatatcagg ctatcaaccc aaaacgtcat   5880
cgatgcggaa aaggcaccag gaggacccta cagacttgga acctcaggat cttgccctaa   5940
cgctaccagt aagagcggat ttttcgcaac aatggcttgg gctgtcccaa aggacaacaa   6000
caaaaatgca acgaacccac taacagtaga agtaccatac atttgtacag aaggggaaga   6060
ccaaatcact gtttgggggt tccattcaga tgacaaaacc caaatgaaga acctctatgg   6120
agactcaaat cctcaaaagt tcacctcatc tgctaatgga gtaaccacac actatgtttc   6180
tcagattggc agcttcccag atcaaacaga agacggagga ctaccacaaa gcggcaggat   6240
tgttgttgat tacatgatgc aaaaacctgg gaaaacagga acaattgtct accaaagagg   6300
tgttttgttg cctcaaaagg tgtggtgcgc gagtggcagg agcaaagtaa taaagggtc   6360 cttgccttta attggtgaag cagattgcct tcatgaaaaa tacggtggat taacaaaag   6420 caagccttac tacacaggag aacatgcaaa agccatagga aattgcccaa tatgggtgaa   6480
aacacctttg aagcttgcca atggaaccaa atatagacct cctgcaaaac tattaaagga   6540
aaggggtttc ttcggagcta ttgctggttt cctagaagga ggatgggaag aatgattgc   6600 aggctggcac ggatacacat ctcacggagc acatggagtg gcagtggcgg cggaccttaa   6660
gagtacgcaa gaagctataa acaagataac aaaaaatctc aattctttga gtgagctaga   6720
agtaaagaat cttcaaagac taagtggtgc catggatgaa ctccacacg aaatactcga   6780 gctggatgag aaagtggatg atctcagagc tgacactata agctcgcaaa tagaacttgc   6840
agtcttgctt tccaacgaag gaataataaa cagtgaagat gagcatctat ggcacttga   6900 gagaaaacta aagaaaatgc tgggtccctc tgctgtagag atagggaatg gatgcttcga   6960
aaccaaacac aagtgcaacc agacctgctt agacaggata gctgctggca cctttaatgc   7020
aggagaattt tctctcccca cttttgattc actgaacatt actgctgcat ctttaaatga   7080
tgatggattg gataaccata ctatactgct ctattactca actgctgctt ctagtttggc   7140
tgtaacattg atgctagcta tttttattgt ttatatggtc tccagagaca cgtttcatg   7200 ctccatctgt ctataagtcg acgtactaga ggatcataat cagccatacc acatttgtag   7260
aggttttact tgctttaaaa aacctcccac acctcccct gaacctgaaa cataaaatga   7320
atgcaattgt tgttgttaac ttgtttattg cagcttataa tggttacaaa taaagcaata   7380
gcatcacaaa tttcacaaat aaagcatttt tttcactgca ttctagttgt ggtttgtcca   7440
aactcatcaa tgtatcttat catgtctgga tctgatcact gcttgagcct agaagatccg   7500
gctgctaaca aagcccgaaa ggaagctgag ttggctgctg tggctagctt tgtttaactt   7560
taagaaggag atacatctag aaatattaat agatcatgga gataattaaa atgataacca   7620
tctcgcaaat aaataagtat tttactgttt tcgtaacagt tttgtaataa aaaaacctat   7680
aaatattccg gattattcat accgtcccac catcggcgc ggatccacca tgctaccttc   7740
aactatacaa acgttaaccc tatttctcac atcagggga gtgttattat cactatatgt   7800
```

```
gtcagcttca ttgtcatact tactatattc ggatatattg ctaaaatttt cacaaacaga    7860
aataactgca ccaataatgc cattggattg tgcaaacgca tcaaatgttc aggctgtgaa    7920
ccgttctgca gcaaaagggg tgacacttct tctcccagaa ccggagtgga catacccteg    7980 tttatcttgc ccgggctcaa cctttcagaa agcactccta attagccccc atagattcgg    8040
agaaaccaaa ggaaactcag ctcccttgat aataagggaa ccttttattg cttgtggacc    8100
aacggaatgc aaacactttg ctctaaccca ttatgcagct caaccagggg gatactacaa    8160
tggaacaaga gaagacagaa acaagctgag gcatctaatt tcagtcaaat gggcaaaat    8220 cccaacagta gaaaactcca ttttccatat ggcagcttgg agcgggtccg catgccatga    8280
tggtaaagaa tggacatata tcggagttga tggccccgac agtaatgcat tactcaaaat    8340
aaaatatgga gaagcatata ctgacacata ccattcctat gcaaaaaaca tcctaaggac    8400
acaagaaagt gcctgcaatt gcatcggggg agattgttat cttatgataa ctgatggccc    8460
agcttcaggg attagtgaat gcagattcct taagattcga gagggccgaa aataaaaga     8520 aatatttcca acaggaagag taaaacatac tgaggaatgc acatgcggat ttgccagcaa    8580
caaaaccata gaatgtgctt gtagagataa cagttacaca gcaaaaagac cctttgtcaa    8640
attaaatgtg gagactgata cagcggaaat aagattgatg tgcacagaga cttatttgga    8700 caccccaga ccaaatgatg gaagcataac agggccttgc gaatctgatg gggacaaagg    8760
gagtggaggc atcaagggag gatttgttca tcaaagaatg catccaaga ttggaaggtg    8820 gtactctcga acgatgtcta aaactaaaag aatggggatg ggactgtatg taaagtatga    8880
tggagaccca tggactgaca gtgaagccct tgctcttagt ggagtaatgg tttcgatgga    8940
agaacctggt tggtattcct ttggcttcga aataaaagat aagaaatgtg atgtcccctg    9000
tattgggata gaaatggtac atgatggtgg gaaaacgact tggcactcag cagcaacagc    9060
catttactgt ttaatgggct caggacaact gctgtgggac actgtcacag gtgttgatat    9120
ggctctgtaa atcgatgaca agcttgtcga gaagtactag aggatcataa tcagccatac    9180
cacatttgta gaggttttac ttgctttaaa aaacctccca cacctccccc tgaacctgaa    9240
acataaaatg aatgcaattg ttgttgttaa cttgtttatt gcagcttata atggttacaa    9300
ataaagcaat agcatcacaa atttcacaaa taaagcattt ttttcactgc attctagttg    9360
tggtttgtcc aaactcatca atgtatctta tcatgtctgg atctgatcac tgcttgagcc    9420
tagaagatcc ggctgctaac aaagcccgaa aggaagctga gttggctgct gggtgcctaa    9480
tgagtgagct aactcacatt aattgcccgg aatattaata gatcatggag ataattaaaa    9540
tgataaccat ctcgcaaata aataagtatt ttactgtttt cgtaacagtt ttgtaataaa    9600 aaacctata aatattccgg attattcata ccgtcccacc atcgggcgcg gatccaccat    9660
gctcgaacca tttcagattc tttcaatttg ttcttttatc ttatcagctc tccatttcat    9720
ggcttggaca ataggcatt tgaatcaaat aaaaagagga ataaacatga aaatacgaat    9780
aaaaggtcca aacaaagaga caataaacag agaggtatca attttgagac acagttacca    9840 aaagaaatc caggccaaag aaacaatgaa ggaagtactc tctgacaaca tggaggtgtt    9900
gagtgaccac ataataattg aggggctttc tgccgaagag ataataaaaa tgggtgaaac    9960
agttttggag atagaagaat tgcattaagt actagaggat cataatcagc cataccacat   10020
ttgtagaggt tttacttgct ttaaaaaacc tcccacacct cccctgaac ctgaaacata    10080 aaatgaatgc aattgttgtt gttaacttgt ttattgcagc ttataatggt tacaaataaa    10140
gcaatagcat cacaaatttc acaaataaag cattttttc actgcattct agttgtggtt   10200
```

-continued

```
tgtccaaact catcaatgta tcttatcatg tctggatctg atcactgctt gagcctagaa    10260
gatccggctg ctaacaaagc ccgaaaggaa gctgagttgg ctgctgccac cgctgagcaa    10320
taactatcat aacccctagg agatccgaac cagataagtg aaatctagtt ccaaactatt    10380
ttgtcatttt taattttcgt attagcttac gacgctacac ccagttccca tctattttgt    10440
cactcttccc taaataatcc ttaaaaactc catttccacc cctcccagtt cccaactatt    10500
ttgtccgccc acagcggggc attttcttc ctgttatgtt tttaatcaaa catcctgcca    10560
actccatgtg acaaaccgtc atcttcggct acttt                              10595
```

<210> SEQ ID NO 4
<211> LENGTH: 8411
<212> TYPE: DNA
<213> ORGANISM: Artificial
<220> FEATURE:
<223> OTHER INFORMATION: multi-epitope papilloma virus-like particle

<400> SEQUENCE: 4

```
ttctctgtca cagaatgaaa attttttctgt catctcttcg ttattaatgt tgtaattga      60 ctgaatatca acgcttattt gcagcctgaa tggcgaatgg gacgcgccct gtagcggcgc     120
attaagcgcg gcgggtgtgg tggttacgcg cagcgtgacc gctacacttg ccagcgccct    180
agcgcccgct cctttcgctt tcttcccttc ctttctcgcc acgttcgccg gctttccccg    240
tcaagctcta aatcggggc tccctttagg gttccgattt agtgctttac ggcacctcga    300
ccccaaaaaa cttgattagg gtgatggttc acgtagtggg ccatcgccct gatagacggt    360
ttttcgccct ttgacgttgg agtccacgtt cttaatagtg gactcttgtt ccaaactgga    420
acaacactca accctatctc ggtctattct tttgatttat aagggattt gccgatttcg    480 gcctattggt taaaaaatga gctgatttaa caaaaattta acgcgaattt taacaaaata    540
ttaacgctta caattaggt ggcacttttc ggggaaatgt gcgcggaacc cctatttgtt    600 tattttcta aatacattca aatatgtatc cgctcatgag acaataaccc tgataaatgc    660
ttcaataata ttgaaaaagg aagagtatga gtattcaaca tttccgtgtc gcccttattc    720 cctttttgc ggcattttgc cttcctgttt ttgctcaccc agaaacgctg gtgaaagtaa    780
aagatgctga agatcagttg ggtgcacgag tgggttacat cgaactggat ctcaacagcg    840
gtaagatcct tgagagtttt cgccccgaag aacgttttcc aatgatgagc acttttaaag    900
ttctgctatg tggcgcggta ttatcccgta ttgacgccgg gcaagagcaa ctcggtcgcc    960
gcatacacta ttctcagaat gacttggttg agtactcacc agtcacagaa aagcatctta   1020
cggatggcat gacagtaaga gaattatgca gtgctgccat aaccatgagt gataacactg   1080
cggccaactt acttctgaca acgatcgag gaccgaagga gctaaccgct tttttgcaca   1140
acatggggga tcatgtaact cgccttgatc gttgggaacc ggagctgaat gaagccatac   1200
caaacgacga gcgtgacacc acgatgcctg tagcaatggc aacaacgttg cgcaaactat   1260
taactggcga actacttact ctagcttccc ggcaacaatt aatagactgg atggaggcgg   1320
ataaagttgc aggaccactt ctgcgctcgg cccttccggc tggctggttt attgctgata   1380
aatctggagc cggtgagcgt gggtctcgcg gtatcattgc agcactgggg ccagatggta   1440
agccctcccg tatcgtagtt atctacacga cggggagtca ggcaactatg gatgaacgaa   1500
atagacagat cgctgagata ggtgcctcac tgattaagca ttggtaactg tcagaccaag   1560
tttactcata tatactttag attgatttaa aacttcattt ttaatttaaa aggatctagg   1620
```

```
tgaagatcct ttttgataat ctcatgacca aaatcccttta acgtgagttt tcgttccact    1680
gagcgtcaga ccccgtagaa aagatcaaag gatcttcttg agatccttt tttctgcgcg      1740 taatctgctg cttgcaaaca aaaaaaccac cgctaccagc ggtggtttgt ttgccggatc     1800
aagagctacc aactcttttt ccgaaggtaa ctggcttcag cagagcgcag ataccaaata     1860
ctgttcttct agtgtagccg tagttaggcc accacttcaa gaactctgta gcaccgccta    1920
catacctcgc tctgctaatc ctgttaccag tggctgctgc cagtgcgat aagtcgtgtc     1980 ttaccgggtt ggactcaaga cgatagttac cggataaggc gcagcggtcg ggctgaacgg    2040
ggggttcgtg cacacagccc agcttggagc gaacgaccta caccgaactg agatacctac    2100
agcgtgagct atgagaaagc gccacgcttc ccgaagggag aaaggcggac aggtatccgg    2160
taagcggcag ggtcggaaca ggagagcgca cgagggagct tccaggggga aacgcctggt    2220
atctttatag tcctgtcggg tttcgccacc tctgacttga gcgtcgattt ttgtgatgct    2280
cgtcaggggg gcggagccta tggaaaaacg ccagcaacgc ggcctttta cggttcctgg     2340 ccttttgctg gccttttgct cacatgttct ttcctgcgtt atcccctgat tctgtggata    2400
accgtattac cgccttttgag tgagctgata ccgctcgccg cagccgaacg accgagcgca   2460
gcgagtcagt gagcgaggaa gcggaagagc gcctgatgcg gtattttctc cttacgcatc    2520
tgtgcggtat ttcacaccgc atagaccagc cgcgtaacct ggcaaaatcg gttacggttg    2580
agtaataaat ggatgccctg cgtaagcggg tgtgggcgga caataaagtc ttaaactgaa    2640 caaatagat ctaaactatg acaataaagt cttaaactag acagaatagt tgtaaactga     2700
aatcagtcca gttatgctgt gaaaaagcat actggacttt tgttatggct aaagcaaact    2760
cttcattttc tgaagtgcaa attgcccgtc gtattaaaga ggggcgtggc caagggcatg    2820
gtaaagacta tattcgcggc gttgtgacaa tttaccgaac aactccgcgg ccgggaagcc    2880
gatctcggct tgaacgaatt gttaggtggc ggtacttggg tcgatatcaa agtgcatcac    2940
ttcttcccgt atgcccaact ttgtatagag agccactgcg ggatcgtcac cgtaatctgc    3000
ttgcacgtag atcacataag caccaagcgc gttggcctca tgcttgagga gattgatgag    3060
cgcggtggca atgccctgcc tccggtgctc gccggagact gcgagatcat agatatagat    3120
ctcactacgc ggctgctcaa acttgggcag aacgtaagcc gcgagagcgc caacaaccgc    3180
ttcttggtcg aaggcagcaa gcgcgatgaa tgtcttacta cggagcaagt tcccgaggta    3240
atcggagtcc ggctgatgtt gggagtaggt ggctacgtct ccgaactcac gaccgaaaag    3300
atcaagagca gcccgcatgg atttgacttg gtcagggccg agcctacatg tgcgaatgat    3360
gcccatactt gagccaccta actttgtttt agggcgactg ccctgctgcg taacatcgtt    3420
gctgctgcgt aacatcgttg ctgctccata acatcaaaca tcgacccacg cgtaacgcg    3480 cttgctgctt ggatgcccga ggcatagact gtacaaaaaa acagtcataa caagccatga    3540
aaaccgccac tgcgccgtta ccaccgctgc gttcggtcaa ggttctggac cagttgcgtg    3600
agcgcatacg ctacttgcat tacagtttac gaaccgaaca ggcttatgtc aactgggttc    3660
gtgccttcat ccgtttccac ggtgtgcgtc acccggcaac cttgggcagc agcgaagtcg    3720
aggcatttct gtcctggctg gcgaacgagc gcaaggtttc ggtctccacg catcgtcagg    3780
cattggcggc cttgctgttc ttctacggca aggtgctgtg cacggatctg cccttgcttc    3840
aggagatcgg tagacctcgg ccgtcgcggc gcttgccggt ggtgctgacc ccggatgaag    3900
tggttcgcat cctcggtttt ctggaaggcg agcatcgttt gttcgcccag gactctagct    3960
atagttctag tggttggcta cagctttgtt tgtactatca acaggttgaa ctgctgatca    4020
```

```
acagatcctc tacgcggccg cggtaccata acttcgtata gcatacatta tacgaagtta    4080
tctggtttaa acgtacccgt agtggctatg cagggcttg ccgccccgac gttggctgcg     4140
agccctgggc cttcacccga acttgggggt tggggtgggg aaaaggaaga aacgcgggcg    4200
tattggtccc aatggggtct cggtggggta tcgacagagt gccagccctg ggaccgaacc    4260
ccgcgtttat gaacaaacga cccaacaccc gtgcgtttta ttctgtcttt ttattgccgt    4320
catagcgcgg gttccttccg gtattgtctc cttccgtgtt tcagttagcc tccccatct    4380 cccggtaccg catgctatgc ataagctttt acagcttgcg cttcttcctc ttagcggtgg    4440
tggaggtgga ggaggtggtg ggggtagcct tgcgcttgcc cagggtgaac ttgggcttgg    4500
ccttcagtcc ggcctgcagc aggaacttgc gacccagggg gaactggtcc aggtcagcgg    4560
agaacttctc cttcaggttg acctcccaga aggtgtactt cttcagggg tcctccttgg     4620 gagcaggggg ggtgtgcttc tggcaagcga tagcctggga ggtgacgaaa cggtaggtgt    4680
cctcgagggt gccaccggga gggggctgca gaccgaagtt ccaatcttcg aggatagtgg    4740
agttcatgga gtggatgtag gtcatcacgt cagcggtcag ggtgatcttg cacagctgga    4800
agatgaactg caggtcgtac tcctcgccgt gacgcaggta ctccttgaag ttggtgttct    4860
tgtaggtagt ctcggaggtg gagatagcag cgcacagaga catgttggtg aacgggtgg    4920 tgtcgaccac ggtcacgaac agctggttgc cccagcagat accgttgttg tgaccctgag    4980
cacgctgcag ccagtagggc ttgttgaaga tctgagcgtc ggaggtgacc atggaaccgg    5040
agggggtagg gaagtagttg ctggaagcca ggttagcggt ggaaccggaa cccttgatgt    5100
acaggtcgtc gggcacgttc tcgcccacag caccagcacg gttgaacagg tgacgcacga    5160
acatctgctc acgacgcagg tagaagaaca gggagtcgcc gtagggctcg gacaccatct    5220
tgatgtagtc ggggtacttg cagatggagg tgcagatgtc caggggcacc tcggacttgt    5280
tagcctgcag ggtggtgaag tccatagcac cgaaaccggt gtccaccatg tcgccgtcct    5340
ggatcacggt gttgatcagc tcgagagggg ggcagtcgcc ggggttcaca gccacgttgg    5400
tgcaggggga acccttgccc cagtgctcgc cgatgggggg cttgcaaccg atcaggcaca    5460
gctgggtctg cttgtagtcc atggagatgc actcgcggtt gtcgacacca gcgttagcag    5520
cgtaagcgga agcgttctcg gtgtcgtcca gcttgttcag caggggtga ccggagatac     5580 cgacacccag gggctggcca cggccgacct ccacgcccac gcaagccac acgaggcgct     5640 gggtgtcagg gttgtagaag gaggtgtcgg ggaaaccgaa cttgttgggg tcggcaggt     5700 ggatacggaa cacacggtac tgcaggccgg acaccttggg caccaggatc ttgttgttgt    5760
tgggcttctt gatggggaag taggggtgac ccacagccag cagacgggag gtgccagcgt    5820
ggtagtagat gttggtacga gccacgtact cgtcggtgga caccaccttg gacacgggca    5880 cgggggggcag gtacacggta gcctcggagg gcagccacag ggacatggtg gcggatccat    5940
cccgggtgat caagtcttcg tcgagtgatt gtaaataaaa tgtaatttac agtatagtat    6000
tttaattaat atacaaatga tttgataata attcttattt aactataata tattgtgttg    6060
ggttgaatta aaggtccgta tactagtatc gattcgcgac ctactccgga atattaatag    6120
atcatggaga taattaaaat gataaccatc tcgcaaataa ataagtattt tactgttttc    6180
gtaacagttt tgtaataaaa aaacctataa atattccgga ttattcatac cgtcccacca    6240
tcgggcgcgg atccgccacc atggctctgt ggcgtccctc cgacaacacc gtgtacctgc    6300 cccctcccctc cgtggctcgt gtggtcaaca ccgacgacta cgtgacccgt acctccatct    6360
```

```
tctaccacgc tggttcctcc cgtctgctga ccgtgggcaa ccccctacttc cgtgtgcccg   6420 ctggcggtgg caacaagcag gacatcccca aggtgtccgc ttaccagtac cgtgtgttcc   6480
gtgtgcagct gcccgacccc aacaagttcg gtctgcccga cacctccatc tacaaccccg   6540
agactcagcg cctcgtgtgg gcttgcgctg tgtcgagat cggtcgtggc cagcccctgg   6600
gtgtcggcct gtccggtcac cccttctaca acaagctgga cgacaccgag tcctcccacg   6660
ctgctacctc caacgtgtcc gaggacgtgc gcgacaacgt gtctgtggac tacaagcaga   6720
cccagctgtg catcctgggt tgcgctcccg ctatcggcga gcactgggct aagggcaccg   6780
cttgcaagtc ccgtcctctg tcccagggcg actgcccccc tctcgagctg aagaacaccg   6840
tgctcgagga cggcgacatg gtggacaccg gttacggtgc tatggacttc agcaccctgc   6900
aggacaccaa gtgcgaggtg cccctggaca tctgccagtc catctgcaag taccccgact   6960
acctgcagat gtccgctgac ccctacggcg actctatgtt cttctgcctg cgtcgtgagc   7020
agctgttcgc tcgtcacttc tggaaccgtg ctggcaccat gggtgacacc gtgccccagt   7080
ccctgtacat caagggcacc ggcatgcgtg cttccccgg ttcctgcgtg tactcccctt   7140
ccccctccgg ttccatcgtg acctccgact cccagctgtt caacaagccc tactggctgc   7200
acaaggctca gggtcacaac aacggtgtct gctggcacaa ccagctgttc gtgaccgtgg   7260
tcgacaccac ccgttccacc aacctgacca tctgcgcttc cacccagtcc cccgtgcccg   7320
gccagtacga cgctaccaag ttcaagcagt actcccgtca cgtggaggag tacgacctgc   7380
agttcatctt ccagctctgc actatcaccc tgaccgctga cgtgatgtcc tacatccact   7440
ccatgaactc ctctatcctc gaagattgga acttcggtgt ccccccctcc cccactacct   7500
ccctggtgga cacttaccgt ttcgtgcagt ccgtggctat cacctgccag aaggacgctg   7560
ctcccgctga gaacaaggac ccctacgaca gctgaagtt ctggaacgtg acctgaagg   7620 agaagttctc cctggacctg gaccagtacc ccctgggtcg caagttcctg gtgcaggctg   7680
gcctgaggcg caagcccacc atcggtcccc gcaagcgttc cgctccctcc gctaccacct   7740
cctccaagcc cgccaagcgt gtgcgtgtgc gcgctcgcaa gtaagctagc aagcttgtcg   7800
agaagtacta gaggatcata atcagccata ccacatttgt agaggtttta cttgctttaa   7860
aaaacctccc acacctcccc ctgaacctga acataaaat gaatgcaatt gttgttgtta   7920
acttgtttat tgcagcttat aatggttaca aataaagcaa tagcatcaca aatttcacaa   7980
ataaagcatt ttttcactg cattctagtt gtggtttgtc caaactcatc aatgtatctt   8040
atcatgtctg gatctgatca ctgcttgagc ctagaagatc cggctgctaa caaagcccga   8100
aaggaagctg agttggctgc tgccaccgct gagcaataac tatcataacc cctaggagat   8160
ccgaaccaga taagtgaaat ctagttccaa actattttgt cattttttaat tttcgtatta   8220 gcttacgacg ctacacccag ttcccatcta ttttgtcact cttccctaaa taatccttaa   8280
aaactccatt tccaccccctc ccagttccca actattttgt ccgccacag cggggcattt   8340 ttcttcctgt tatgttttta atcaaacatc ctgccaactc catgtgacaa accgtcatct   8400
tcggctactt t                                                        8411
```

<210> SEQ ID NO 5  
<211> LENGTH: 8445  
<212> TYPE: DNA  
<213> ORGANISM: Artificial  
<220> FEATURE:  
<223> OTHER INFORMATION: multi-epitope papilloma virus-like particle

<400> SEQUENCE: 5

```
ttctctgtca cagaatgaaa attttttctgt catctcttcg ttattaatgt ttgtaattga    60
ctgaatatca acgcttattt gcagcctgaa tggcgaatgg gacgcgccct gtagcggcgc   120
attaagcgcg gcgggtgtgg tggttacgcg cagcgtgacc gctacacttg ccagcgccct   180
agcgcccgct cctttcgctt tcttcccttc ctttctcgcc acgttcgccg gctttccccg   240
tcaagctcta aatcgggggc tccctttagg gttccgattt agtgctttac ggcacctcga   300
ccccaaaaaa cttgattagg gtgatggttc acgtagtggg ccatcgccct gatagacggt   360
ttttcgccct ttgacgttgg agtccacgtt cttaatagtg gactcttgtt ccaaactgga   420
acaacactca accctatctc ggtctattct tttgatttat aagggatttt gccgatttcg   480
gcctattggt taaaaaatga gctgatttaa caaaaattta acgcgaattt taacaaaata   540
ttaacgctta caatttaggt ggcacttttc ggggaaatgt gcgcggaacc cctatttgtt   600
tatttttcta aatacattca aatatgtatc cgctcatgag acaataaccc tgataaatgc   660
ttcaataata ttgaaaaagg aagagtatga gtattcaaca tttccgtgtc gcccttattc   720
ccttttttgc ggcattttgc cttcctgttt ttgctcaccc agaaacgctg gtgaaagtaa   780
aagatgctga agatcagttg ggtgcacgag tgggttacat cgaactggat ctcaacagcg   840
gtaagatcct tgagagtttt cgccccgaag aacgttttcc aatgatgagc acttttaaag   900
ttctgctatg tggcgcggta tatcccgta ttgacgccgg gcaagagcaa ctcggtcgcc   960
gcatacacta ttctcagaat gacttggttg agtactcacc agtcacagaa aagcatctta  1020
cggatggcat gacagtaaga gaattatgca gtgctgccat aaccatgagt gataacactg  1080
cggccaactt acttctgaca acgatcggag gaccgaagga gctaaccgct tttttgcaca  1140
acatggggga tcatgtaact cgccttgatc gttgggaacc ggagctgaat gaagccatac  1200
caaacgacga gcgtgacacc acgatgcctg tagcaatggc aacaacgttg cgcaaactat  1260
taactggcga actacttact ctagcttccc ggcaacaatt aatagactgg atggaggcgg  1320
ataaagttgc aggaccactt ctgcgctcgg cccttccggc tggctggttt attgctgata  1380
aatctggagc cggtgagcgt gggtctcgcg gtatcattgc agcactgggg ccagatggta  1440
agccctcccg tatcgtagtt atctacacga cggggagtca ggcaactatg gatgaacgaa  1500
atagacagat cgctgagata ggtgcctcac tgattaagca ttggtaactg tcagaccaag  1560
tttactcata tatactttag attgatttaa aacttcattt ttaatttaaa aggatctagg  1620
tgaagatcct tttgataat ctcatgacca aaatccctta acgtgagttt cgttccact    1680 gagcgtcaga ccccgtagaa aagatcaaag gatcttcttg agatcctttt ttctgcgcg   1740 taatctgctg cttgcaaaca aaaaaaccac cgctaccagc ggtggtttgt ttgccggatc   1800
aagagctacc aactcttttt ccgaaggtaa ctggcttcag cagagcgcag ataccaaata   1860
ctgttcttct agtgtagccg tagttaggcc accacttcaa gaactctgta gcaccgccta   1920
catacctcgc tctgctaatc ctgttaccag tggctgctgc cagtggcgat aagtcgtgtc   1980
ttaccgggtt ggactcaaga cgatagttac cggataaggc gcagcggtcg ggctgaacgg   2040 gggggttcgtg cacacagccc agcttggagc gaacgaccta caccgaactg agatacctac   2100
agcgtgagct atgagaaagc gccacgcttc ccgaagggag aaaggcggac aggtatccgg   2160
taagcggcag ggtcggaaca ggagagcgca cgagggagct ccaggggga acgcctggt    2220 atctttatag tcctgtcggg tttcgccacc tctgacttga gcgtcgattt ttgtgatgct   2280
cgtcaggggg gcggagccta tggaaaaacg ccagcaacgc ggcctttta cggttcctgg    2340
```

```
ccttttgctg gccttttgct cacatgttct ttcctgcgtt atcccctgat tctgtggata    2400
accgtattac cgcctttgag tgagctgata ccgctcgccg cagccgaacg accgagcgca    2460
gcgagtcagt gagcgaggaa gcggaagagc gcctgatgcg gtattttctc cttacgcatc    2520
tgtgcggtat ttcacaccgc atagaccagc cgcgtaacct ggcaaaatcg gttacggttg    2580
agtaataaat ggatgccctg cgtaagcggg tgtgggcgga caataaagtc ttaaactgaa    2640
caaaatagat ctaaactatg acaataaagt cttaaactag acagaatagt tgtaaactga    2700
aatcagtcca gttatgctgt gaaaaagcat actggacttt tgttatggct aaagcaaact    2760
cttcattttc tgaagtgcaa attgcccgtc gtattaaaga ggggcgtggc caagggcatg    2820
gtaaagacta tattcgcggc gttgtgacaa tttaccgaac aactccgcgg ccgggaagcc    2880
gatctcggct tgaacgaatt gttaggtggc ggtacttggg tcgatatcaa agtgcatcac    2940
ttcttcccgt atgcccaact tgtatagag agccactgcg ggatcgtcac cgtaatctgc    3000
ttgcacgtag atcacataag caccaagcgc gttggcctca tgcttgagga gattgatgag    3060
cgcggtggca atgccctgcc tccggtgctc gccggagact gcgagatcat agatatagat    3120
ctcactacgc ggctgctcaa acttgggcag aacgtaagcc gcgagagcgc caacaaccgc    3180
ttcttggtcg aaggcagcaa gcgcgatgaa tgtcttacta cggagcaagt tcccgaggta    3240
atcggagtcc ggctgatgtt gggagtaggt ggctacgtct ccgaactcac gaccgaaaag    3300
atcaagagca gcccgcatgg atttgacttg gtcaggccg agcctacatg tgcgaatgat    3360
gcccatactt gagccaccta actttgtttt agggcgactg ccctgctgcg taacatcgtt    3420
gctgctgcgt aacatcgttg ctgctccata acatcaaaca tcgacccacg cgtaacgcg    3480 cttgctgctt ggatgcccga ggcatagact gtacaaaaaa acagtcataa caagccatga    3540
aaaccgccac tgcgccgtta ccaccgctgc gttcggtcaa ggttctggac cagttgcgtg    3600
agcgcatacg ctacttgcat tacagtttac gaaccgaaca ggcttatgtc aactgggttc    3660
gtgccttcat ccgtttccac ggtgtgcgtc acccggcaac cttgggcagc agcgaagtcg    3720
aggcatttct gtcctggctg gcgaacgagc gcaaggtttc ggtctccacg catcgtcagg    3780
cattggcggc cttgctgttc ttctacggca aggtgctgtg cacggatctg cccttgcttc    3840
aggagatcgg tagacctcgg ccgtcgcggc gcttgccggt ggtgctgacc ccggatgaag    3900
tggttcgcat cctcggtttt ctggaaggcg agcatcgttt gttcgcccag gactctagct    3960
atagttctag tggttggcta cagctttgtt tgtactatca acaggttgaa ctgctgatca    4020
acagatcctc tacgcggccg cggtaccata acttcgtata gcatacatta tacgaagtta    4080
tctggtttcg acctactccg gaatattaat agatcatgga gataattaaa atgataacca    4140
tctcgcaaat aaataagtat tttactgttt tcgtaacagt tttgtaataa aaaaccctat    4200
aaatattccg gattattcat accgtcccac catcgggcgc ggatccgcca ccatgtccct    4260
gtggctgccc tccgaggcta ccgtgtacct gccccccgtg cccgtgtcca aggtggtgtc    4320
caccgacgag tacgtggctc gtaccaacat ctactaccac gctggcacct cccgtctgct    4380
ggctgtgggt caccccctact tccccatcaa gaagcccaac aacaacaaga tcctggtgcc    4440
caaggtgtcc ggcctgcagt accgtgtgtt ccgtatccac ctgcccgacc caacaagtt    4500 cggtttcccc gacacctcct tctacaaccc tgacacccag cgcctcgtgt gggcttgcgt    4560
gggcgtggag gtcggccgtg gccagcccct gggtgtcggt atctccggtc accccctgct    4620
gaacaagctg gacgacaccg agaacgcttc cgcttacgct gctaacgctg tgtcgacaa    4680 ccgcgagtgc atctccatgg actacaagca gacccagctg tgcctgatcg gttgcaagcc    4740
```

```
ccccatcggc gagcactggg gcaagggttc cccctgcacc aacgtggctg tgaaccccgg    4800
cgactgcccc cctctcgagc tgatcaacac cgtgatccag gacggcgaca tggtggacac    4860
cggtttcggt gctatggact tcaccaccct gcaggctaac aagtccgagg tgcccctgga    4920
catctgcacc tccatctgca gtacccccga ctacatcaag atggtgtccg agccctacgg    4980
cgactccctg ttcttctacc tgcgtcgtga gcagatgttc gtgcgtcacc tgttcaaccg    5040
tgctggtgct gtgggcgaga acgtgcccga cgacctgtac atcaagggtt ccggttccac    5100
cgctaacctg gcttccagca actacttccc taccccctcc ggttccatgg tcacctccga    5160
cgctcagatc ttcaacaagc cctactggct gcagcgtgct cagggtcaca caacggtat    5220
ctgctggggc aaccagctgt tcgtgaccgt ggtcgacacc acccgttcca ccaacatgtc    5280
tctgtgcgct gctatctcca cctccgagac tacctacaag aacaccaact tcaaggagta    5340
cctgcgtcac ggcgaggagt acgacctgca gttcatcttc cagctgtgca agatcaccct    5400
gaccgctgac gtgatgacct acatccactc catgaactcc actatcctcg aagattggaa    5460
cttcggtctg cagcccccctc ccggtggcac cctcgaggac acctaccgtt cgtcacctc    5520
ccaggctatc gcttgccaga agcacacccc ccctgctccc aaggaggacc ccctgaagaa    5580
gtacaccttc tgggaggtca acctgaagga gaagttctcc gctgacctgg accagttccc    5640
cctgggtcgc aagttcctgc tgcaggccgg actgaaggcc aagcccaagt tcaccctggg    5700
caagcgcaag gctaccccca ccacctcctc cacctccacc accgctaaga ggaagaagcg    5760
caagctgtaa aagcttgtcg agaagtacta gaggatcata atcagccata ccacatttgt    5820
agaggtttta cttgctttaa aaaacctccc acacctcccc ctgaacctga aacataaaat    5880
gaatgcaatt gttgttgtta acttgtttat tgcagcttat aatggttaca ataaagcaa    5940
tagcatcaca aatttcacaa ataaagcatt tttttcactg cattctagtt gtggtttgtc    6000
caaactcatc aatgtatctt atcatgtctg gatctgatca ctgcttgagc ctagaagatc    6060
cggctgctaa caaagcccga aggaagctg agttggctgc tgtggctagc tttgtttaac    6120
tttaagaagg atacatctc agaaatatta atagatcatg gagataatta aaatgataac    6180
catctcgcaa ataaataagt atttttactgt tttcgtaaca gttttgtaat aaaaaaacct    6240
ataaatattc cggattattc ataccgtccc accatcgggc gcggatccgc caccatggct    6300
ctgtggcgtc cctccgacaa caccgtgtac ctgcccccctc cctccgtggc tcgtgtggtc    6360
aacaccgacg actacgtgac ccgtacctcc atcttctacc acgctggttc ctcccgtctg    6420
ctgaccgtgg caaccccta cttccgtgtg cccgctggcg gtggcaacaa gcaggacatc    6480
cccaaggtgt ccgcttacca gtaccgtgtg ttccgtgtgc agctgcccga ccccaacaag    6540
ttcggtctgc ccgacacctc catctacaac cccgagactc agcgcctcgt gtgggcttgc    6600
gctggtgtcg agatcggtcg tggccagccc ctgggtgtcg gcctgtccgg tcacccttc    6660
tacaacaagc tggacgacac cgagtcctcc acgctgctaa cctccaacgt gtccgaggac    6720
gtgcgcgaca acgtgtctgt ggactacaag cagacccagc tgtgcatcct gggttgcgct    6780
cccgctatcg gcgagcactg ggctaagggc accgcttgca agtcccgtcc tctgtcccag    6840
ggcgactgcc cccctctcga gctgaagaac accgtgctcg aggacggcga catggtggac    6900
accggttacg gtgctatgga cttcagcacc ctgcaggaca ccaagtgcga ggtgccctg    6960
gacatctgcc agtccatctg caagtacccc gactacctgc agatgtccgc tgaccccta    7020
ggcgactcta tgttcttctg cctgcgtcgt gagcagctgt tcgctcgtca cttctggaac    7080
```

-continued

```
cgtgctggca ccatgggtga caccgtgccc cagtccctgt acatcaaggg caccggcatg   7140
cgtgcttccc ccggttcctg cgtgtactcc ccttccccct ccggttccat cgtgacctcc   7200
gactcccagc tgttcaacaa gccctactgg ctgcacaagg ctcagggtca caacaacggt   7260
gtctgctggc acaaccagct gttcgtgacc gtggtcgaca ccacccgttc caccaacctg   7320
accatctgcg cttccaccca gtcccccgtg cccggccagt acgacgctac caagttcaag   7380
cagtactccc gtcacgtgga ggagtacgac ctgcagttca tcttccagct ctgcactatc   7440
accctgaccg ctgacgtgat gtcctacatc cactccatga actcctctat cctcgaagat   7500
tggaacttcg gtgtccccc tccccccact acctccctgg tggacactta ccgtttcgtg   7560
cagtccgtgg ctatcacctg ccagaaggac gctgctcccg ctgagaacaa ggacccctac   7620
gacaagctga agttctggaa cgtggacctg aaggagaagt tctccctgga cctggaccag   7680
taccccctgg gtcgcaagtt cctggtgcag gctggcctga ggcgcaagcc caccatcggt   7740
ccccgcaagc gttccgctcc ctccgctacc acctcctcca agcccgccaa gcgtgtgcgt   7800
gtgcgcgctc gcaagtaagc tagcaagctt gtcgagaagt actagaggat cataatcagc   7860
cataccacat ttgtagaggt tttacttgct ttaaaaaacc tcccacacct ccccctgaac   7920
ctgaaacata aaatgaatgc aattgttgtt gttaacttgt ttattgcagc ttataatggt   7980
tacaaataaa gcaatagcat cacaaatttc acaaataaag catttttttc actgcattct   8040
agttgtggtt tgtccaaact catcaatgta tcttatcatg tctggatctg atcactgctt   8100
gagcctagaa gatccggctg ctaacaaagc ccgaaaggaa gctgagttgg ctgctgccac   8160
cgctgagcaa taactatcat aaccccctagg agatccgaac cagataagtg aaatctagtt   8220
ccaaactatt ttgtcatttt taattttcgt attagcttac gacgctacac ccagttccca   8280
tctattttgt cactcttccc taaataatcc ttaaaaactc catttccacc cctcccagtt   8340
cccaactatt ttgtccgccc acagcggggc atttttcttc ctgttatgtt tttaatcaaa   8400
catcctgcca actccatgtg acaaaccgtc atcttcggct acttt                   8445
```